(12) United States Patent
Fang et al.

(10) Patent No.: US 11,340,213 B2
(45) Date of Patent: May 24, 2022

(54) APPARATUS FOR DETECTING ANALYTE IN A LIQUID SAMPLE AND METHOD THEREOF

(71) Applicants: Healgen Scientific Limited, Houston, TX (US); Zhejiang Orient Gene Biotech Co., LTD., Huzhou (CN)

(72) Inventors: Jianqiu Fang, Houston, TX (US); Siyu Lei, Zhejiang (CN)

(73) Assignees: HEALGEN SCIENTIFIC LIMITED, Houston, TX (US); ZHEJIANG ORIENT GENE BIOTECH CO., LTD, Anji (CN)

( * ) Notice: Subject to any disclaimer, the term of this patent is extended or adjusted under 35 U.S.C. 154(b) by 522 days.

(21) Appl. No.: 15/611,327

(22) Filed: Jun. 1, 2017

(65) Prior Publication Data

US 2018/0011079 A1 Jan. 11, 2018

(30) Foreign Application Priority Data

Jul. 8, 2016 (CN) .......................... 201610535201.0
Jul. 8, 2016 (CN) .......................... 201610536307.2

(Continued)

(51) Int. Cl.
*G01N 33/493* (2006.01)
*B01L 3/00* (2006.01)
(Continued)

(52) U.S. Cl.
CPC ......... *G01N 33/493* (2013.01); *A61B 10/007* (2013.01); *A61B 10/0096* (2013.01);
(Continued)

(58) Field of Classification Search
CPC ........... B01L 3/50825; B01L 2200/145; B01L 2300/046; B01L 2200/143;
(Continued)

(56) References Cited

U.S. PATENT DOCUMENTS

| 5,238,130 A | * | 8/1993 | Marques | ............. | B65D 50/046 |
| | | | | | 215/211 |
| 2006/0186075 A1 | | 8/2006 | Rainey et al. | | |

(Continued)

FOREIGN PATENT DOCUMENTS

| CN | 204882557 U | 12/2015 |
| EP | 2921232 A2 | 9/2015 |
| EP | 2921232 A3 | 1/2016 |

OTHER PUBLICATIONS

Extended European Search Report dated Nov. 13, 2017 in European Application Serial No. 17177973.9.

*Primary Examiner* — Dennis White
(74) *Attorney, Agent, or Firm* — Nz Carr Law Office LLP

(57) ABSTRACT

The present invention provides an apparatus for detecting the presence or absence of an analyte in liquid sample, including: a collection chamber, including an opening for collecting a liquid sample; a testing element for testing the analyte in liquid sample; and a cover for covering the opening of the collection chamber; wherein the apparatus further includes a prompting device for prompting if the cover is covered to a specified location, and the prompting device shall at least includes a first element and a second element, the first element is in contact with the second element, wherein one element vibrates to produce a sound. In some preferred ways, the second element produces friction with the first element, to cause one of the elements to generate vibrations. The apparatus in the present invention can allow the prompting sound to be clear and loud.

13 Claims, 16 Drawing Sheets

(30) Foreign Application Priority Data

Jul. 8, 2016 (CN) .......................... 201620716853.X
Jul. 8, 2016 (CN) .......................... 201620718552.0

(51) Int. Cl.
*G01N 33/94* (2006.01)
*A61B 10/00* (2006.01)
*B65D 41/04* (2006.01)

(52) U.S. Cl.
CPC ............... *B01L 3/502* (2013.01); *B01L 3/508* (2013.01); *B01L 3/50853* (2013.01); *B65D 41/0471* (2013.01); *G01N 33/94* (2013.01); *G01N 33/946* (2013.01); *G01N 33/948* (2013.01); *G01N 33/9486* (2013.01); *A61B 2010/0003* (2013.01); *A61B 2010/0009* (2013.01); *B01L 2200/025* (2013.01); *B01L 2200/141* (2013.01); *B01L 2200/143* (2013.01); *B01L 2200/145* (2013.01); *B01L 2300/041* (2013.01); *B01L 2300/046* (2013.01); *B01L 2300/0609* (2013.01); *B01L 2300/0627* (2013.01); *B01L 2300/0663* (2013.01); *B01L 2300/0825* (2013.01); *B01L 2300/0832* (2013.01); *B01L 2300/0848* (2013.01); *B01L 2300/123* (2013.01)

(58) Field of Classification Search
CPC ........... B01L 2400/0433; B01L 3/5023; B01L 3/502; B01L 3/508; B01L 3/50853; B01L 2200/025; B01L 2200/141; B01L 2300/041; B01L 2300/0609; B01L 2300/0627; B01L 2300/0663; B01L 2300/0825; B01L 2300/0832; B01L 2300/0848; B01L 2300/123; B65D 55/02; B65D 2251/01; B65D 41/0471; B65D 55/024; G01N 33/493; G01N 33/94; G01N 33/946; G01N 33/948; G01N 33/9486; A61B 10/007; A61B 5/14507; A61B 5/7405; A61B 10/0096; A61B 2010/0003; A61B 2010/0009
See application file for complete search history.

(56) References Cited

U.S. PATENT DOCUMENTS

| 2013/0004940 | A1 | 1/2013 | Hu et al. | |
| 2013/0068649 | A1* | 3/2013 | Chen | B65D 55/024 206/459.1 |
| 2014/0046215 | A1 | 2/2014 | Hu et al. | |
| 2017/0349342 | A1* | 12/2017 | Girardot | B65D 41/0492 |

* cited by examiner

APPARATUS FOR DETECTING ANALYTE IN A LIQUID SAMPLE AND METHOD THEREOF

RELATED APPLICATIONS

This application claims priority to CN 201610535201.0, filed Jul. 8, 2016; CN 201610536307.2, filed Jul. 8, 2016; CN 201610535365.3, filed Jul. 8, 2016; CN 201621134130.5, filed Oct. 9, 2016; CN 201620716853.X, filed Jul. 8, 2016 and CN 201620718552.0, filed Jul. 8, 2016, each of which are incorporated herein in their entirety by reference.

FIELD OF THE INVENTION

The present invention relates to an apparatus for detecting analyte in a liquid sample and method thereof.

BACKGROUND

The following background art is provided to assist readers in understanding the present invention rather than a prior art.

At present, illegal drug abuse has become a recognized and increasingly worsening social problem. In 2003, the survey conducted by the US Department of Health and Human Services revealed that about 19.5 million Americans or 8.2% of people over the age of 12 are taking illegal drugs. "Recent use of illegal drugs" refers to the use of an illegal drug within one month before the US Department of Health and Human Services conducted a survey. *Cannabis* is found to be the most commonly used illegal drugs, accounting for 6.2% (14.6 million). Now about 2.30 million people (1.0%) are using cocaine, 604,000 people use Crack, and 1 million people are using hallucinogens, and it is estimated that 119,000 people are using heroin. With the development of the times, many new drugs are emerging, and it has become one of the world's important social problems.

In order to fight against the drug abuse monitor this social problem, the drug testing has become a standard test procedure in various industries such as hiring, education, sports, and law enforcement, etc. To promote this effort, the drug testing industry has formed. This industry has provided a wide range of drug testing products. The urine sample collection cup for sample analysis is a classic testing product. These devices may be complex, difficult or dirty for users, or may cause the problem of adulteration in the sample to conceal the use of illegal drugs recently. In addition, the urine samples cannot be collected in some cases, for example, on the roadside or in the public places.

It has become a very common method to collect liquid samples such as urine using a detection apparatus and determine if there is specific analyte (such as drugs and/or their metabolites, or disease-related markers). For this kind of device, usually the samples are required to be collected in the sample container, and relevant technicians insert a test strip and immerse part of the test strip in the sample, then take out the test strip for reading the results. Technicians may be exposed to samples to endanger their health or contaminate the samples. In order to avoid such risk, it is necessary to add the sealed cover on the sample collection container. At present there are a variety of closed devices, for example, the devices disclosed in U.S. Pat. Nos. 4,976,923, 5,429,804, and 6,726,879. The test strips are secured to the lid of the detection apparatus. When used, the container is turned over or tilted to allow the samples to immerse the test strips for testing. The U.S. Patent Application Publication No. US2003/0027359A1 published on Feb. 6, 2003 disclosed a urine cup for detection. For the urine cup for detection, the push rod pushes the piston to move when the cup opening is covered by the lid and make the fluid samples to flow out of the cup chamber and wet the detection element. The Chinese published patent application 200510113977.5 discloses a urine cup for detection. This kind of urine cup can start the liquid to flow from the collection chamber to the detection chamber after the lid is covered to the opening of the cup, to initiate the start of testing. The urine cup starts the testing after the lid is covered to the opening of the cup.

Many other sample collection and testing devices are inefficient in extracting samples from the collection device, with many problems, such as environmental contamination caused by leakage of samples, or the test results are affected by less or more samples collected, or the detection is complicated with a number of operating steps. Many of these devices are very complex in the design and manufacturing, requiring expensive materials. Therefore, it is necessary to collect and test samples with better method and apparatus.

Recently, this detection apparatus has been increasingly used by ordinary families or non-professional organizations. Since these test evaluations are designed for non-professionals, these detection apparatuses should be simple to operate and ensure the accuracy of the test results. Therefore, it is urgent to have a kind of detection apparatus with simple operation and accurate and reliable test results. The present invention is to provide a detection apparatus that meets such needs.

SUMMARY

The present invention provides a simple detection apparatus. Specifically, it provides a urinal cup for testing that is easy to operate. When the lid is covered to the opening of the cup, the prompting device on the urine cup will prompt if the lid is covered to the specified location. On the one hand, when the lid is covered to the opening of the cup, the degree of tightness of the lid covered to the opening of cup may vary when operated by different operators especially non-professionals, which may cause unable to seal the opening of the cup and possibility of leakage. For the present invention, a prompting device is arranged on the detection apparatus, when the lid is covered to the specified location of the collection chamber (the opening of the collection chamber can be adequately sealed by the cover in the location), the prompting device prompts that the opening of the collection chamber is sealed by the lid and operators need not cover the cover again. By this way, the opening of each apparatus can be fully sealed without fear of leakage.

On the other hand, in some apparatus, once the lid is closed to the opening of the collection chamber, the liquid sample in the collection chamber will contact with the testing element for testing; at this time, it is required to start to calculate the time, wait for a period of time and read the test results in the detection region of the testing element. When operated by different operators, since the starting time is not consistent, without a unified standard, the test results may be different for different operators. The present invention provides a detection apparatus, and when the lid is covered to the specified location of the collection chamber, the prompting device gives prompt information, such as a sound, to tell the operators the time to wait for the test results from testing element.

On one hand, the present invention provides an apparatus for detecting the presence or absence of an analyte in liquid sample, including: a collection chamber, including an opening for collecting a liquid sample; a testing element for testing the analyte in liquid sample; and a cover for covering the opening of the collection chamber; wherein the apparatus further includes a prompting device for prompting if the cover is covered to a specified location.

In some preferred ways, when the cover is covered to a specified location, the prompting device prompts that the opening of the collection chamber has been sealed, or when the cover is covered to the specified location, the prompting device prompts to the time to wait for the test results from testing element.

In some preferred ways, the prompting device gives prompts by making a sound. In some specific ways, the prompting device includes one or more elements, for example, the first and the second elements, which can give sounds by elastic deformation. In some preferred ways, specifically, the prompting device includes a first and a second elements, when the first element is in contact with the second element and one of them is deformed such as the first element, the two elements are in contact with each other to generate elastic deformations of both or one element, to rebound and collide each other to make a sound to give prompt, for example, when the first element is deformed, to collide with the first element, or one element has a self-vibration after a deformation occurs, to make a sound. In some preferred ways, the two elements contact each with to produce friction and make sound, to give prompt, for example, when the first element and the second element contact each with to produce friction, and one element for example the first element produces vibration to make a sound.

"Collision" refers to contact in a short period of time suddenly after separated by a certain distance, to make a sound. The sound produced by friction is that two elements have been in contact with each other to do relative movement, to drive two elements to produce surface contact friction and make a sound with the movement, which does not need to separate, or the sound is made by one or both of the mechanism of "mutual collision" and "mutual friction". Generally for the mechanism of sound generation, whether mutual collision, friction or beating, one or two elements can vibrate to make sounds, preferably, one of the elements vibrates to make sound, or two elements vibrate, and the superposition effect of the sound waves makes the sound louder or more pleasing.

In a specific way, the prompting device includes an elastic element, for example, a first element; and a non-elastic element, for example, a second element, when the elastic element passes through the non-elastic element, with the blocking or hindering of the non-elastic element, the elastic element produces elastic deformation; when the blocking force disappears, the elastic element has the power to develop to the original state, to collide with the blocked non-elastic element and make a sound. The terms "elastic element" and "non-elastic element" as used herein are relative concept. In terms of setting, generally the elastic modulus of the elastic element is less than the elastic modulus of the non-elastic element. For example, the plastic is used as an elastic element, and metal such as iron, steel or lead is used as a non-elastic element, in this way, with the mutual force of plastic and non-elastic element, the elastic modulus of elastic element is less than that of the non-elastic element, when they have the same mutual force, the elastic element is more likely to change in shape, and when the force disappears in an instant, the elastic element needs to be restored to the original state, thereby beating or vibrating to make a sound. The force exerted on the element where the elastic deformation occurs is generally less than the inherent elasticity limit of the element, so that they can recover themselves when the external force disappears. Alternatively, both elastic element and non-elastic element are plastic materials.

In some preferred ways, there is one elastic element, such as a first element, and two non-elastic elements, such as the second and third elements, when the elastic element passes through non-elastic elements, one non-elastic element, e.g. the second element, hinders or blocks the elastic element, which causes the deformation of the elastic element, then the elastic element collides with another non-elastic element, e.g. the second element to make a sound. Or there is one elastic element and one non-elastic element, when the elastic element through the non-elastic element, the elastic element is subject to change in shape due to the resistance, and once the resistance disappears, the elastic element may rebound to collide with the resistance element to make a sound.

In some other preferred ways, the two elements do not necessarily need to be an elastic element, while the other is a non-elastic element. The material of the two elements may be elastic elements, or none is elastic element, but due to different physical size, under the same interaction force, one element has elastic deformation and another element does not have deformation. The interaction force is different due to different force fulcrum of the two elements, for example, for the plastics with the same material, their thickness is the same but their length is different, the shorter one is used as a resistance element, and the longer one is used as a deformed element, when the long element moves relative to the short element, once they are in contact, due to the same interaction force, the longer element is deformed but the shorter one is almost not deformed, thus, when the longer element passes through the shorter one, due to deformation, it needs to restore to its original state, to collide with the shorter one to make a sound. At this time, the two elements may be of the same material, but due to different size and force, one is greatly deformed and the other is almost not deformed, or the longer element may vibrate itself and make sound after deformation, or when the long element is in contact with the short element, they produce friction each other to make the longer element to vibrate and make a sound, the long element is easy to produce deformation or vibration than the short element. When the two elements have the same length and material, and same contact force, but since the surface is rough with great friction, it is possible to make one element to make a sound.

More preferably, an elastic element or a long element, for example, a first element, may be located on a cover, for example, an outer edge of a cover; a non-elastic element or a short element, for example, a second element and/or third element, may be located on the outer wall surface of the cup. In a more specific embodiment, the long element and/or elastic element form an angle with the short element and/or non-elastic element, for example, 90 degrees, 60 degrees, 45 degrees, 30 degrees, or 25 degrees. With such setting of angle, during the mutual movement of the long element and/or elastic element with the short element and/or non-elastic element, they will contact each other in a position, to make a sound. In a preferred embodiment, the long element and/or elastic element is arranged perpendicularly to the short element and/or non-elastic element. Of course, alternatively, the elastic element or long component can be located on the cup body, e.g. the outer edge of the cup body; and the non-elastic elements or short element can be located on the cover.

In some preferred ways, the long element and/or elastic element are arranged on the cover and parallel to the central axis of the cover, the short element and/or non-elastic element are arranged on the cup body, perpendicular to the central body of the cup body. In some preferred embodiments, the vertical length of the long element is greater than the length of the short element. In some preferred embodiments, one end of the long element is located in a chamber of the cover and extends outwardly from the chamber, slightly above the opening of the chamber. In some preferred embodiments, the region where the long element is elastically deformed is longer or greater than the region where the long element is in contact with the short element. In this way, the region with actual deformation of the long element is easy to deform compared to the short element, when they produce friction, the region with actual vibration for the long element is greater than that of the short element, to facilitate to make a sound.

In some preferred ways, the camber on the cover is located on the outer peripheral edge of the cover, and as the cover rotates, the long element also moves with the cover. In some preferred embodiments, the short element is located on the outer wall of the cup body. More specifically, it is located on the plane of the ring edge of the cup body extending outwardly, for example, the skirt. In some preferred ways, the ring edge has a certain angle from the centerline of the cup body, for example, 10 degrees, 20 degrees, 30 degrees, 45 degrees, 60 degrees, 70 degrees, or 90 degrees. The short element or non-elastic element is located on the plane of the ring edge. Here, the short element or the non-elastic element may be provided separately on the cup body of the injection modeling, may be protruded upwardly from the plane of the ring edge to form a protruding rib, which may be 0.1 mm-1 mm or 2-3 mm high, so long as the long element can contact with the rib transversely when moving to a certain position.

In other specific embodiments, the non-elastic element is made of ABS material; elastic element is made of PP material. Alternatively, when the elastic element passes through the non-elastic element and beat the non-elastic element, the elastic element is prevented from being moved by the non-elastic element so that it can not move clockwise relative to the cup body. In another alternative embodiment, when the elastic element passes through the non-elastic element, the elastic element can move clockwise relative to the cover. Alternatively, the way that the cover covers to the opening of the collection chamber is to seal the opening of the collection chamber by the cover through rotation, the opening includes the external thread matching with the cover, and the cover includes the internal thread that matches the opening.

In another aspect, the present invention provides a method of detecting analyte in a sample, including providing a detection apparatus, including: a collection chamber including an opening for collecting a liquid sample, a testing element for testing the analyte in liquid sample, and a cover for covering the opening of the collection chamber; The cover is covered to the opening of the collection chamber and one prompting device on detection apparatus prompts whether the cover is closed to the specified location. In one way, the prompting device prompts by making a sound. In another way, once you hear the prompting device to give a prompt, stop continuing to cover the cover to the collection chamber's opening. In a specific way, the cover closes the opening of the collection chamber in a rotation way, and when you hear the prompting device, it is prompted to stop the cover. In addition, in a way, once you hear the prompting device to give a prompt, start calculating the time to wait for the test results from testing element. In another way, once you hear the prompting device to give a prompt, start calculating the time to wait for the test results from testing element, and stop rotating the cover.

The present invention provides a method for detecting analyte in a sample including: providing a detection apparatus including a collection chamber containing an opening; a testing element; and a cover for sealing the opening of the collection chamber through rotation relative to collection chamber, wherein the apparatus furthers includes a prompting device that prompts whether the cover is rotated to the specified location; rotating the cover until the prompting device gives prompt.

In some preferred ways, when the prompting device gives prompt, the rotation is stopped. Alternatively, when the prompting device gives prompt, it begins to calculate the time to wait for the test results from testing element. In a specific way, the prompting device gives prompt by making a sound.

In another aspect, the present invention provides a detection apparatus, including: a collection chamber including an opening for preparing a liquid sample; a testing element for testing analyte in a liquid sample; and a cover to cover the opening of the collection chamber; wherein the cover includes a first element, and the cover body includes a second element. When the first element is in contact with the second element, they produce friction to make a sound. In some preferred embodiments, the sound is made through friction between the first element and the second element during the relative movement. In some preferred embodiments, the movement of the cover relative to the cup body drives the movement of the first element relative to the second element. In some preferred embodiments, the movement of the cover relative to the cup body is a relative rotational motion. In some preferred embodiments, the friction between the first element and the second element makes the first element easy to deform or vibrate, to make a sound.

In all of the above specific embodiments, the structures making a sound, for example an elastic element and a non-elastic element, or a long element and a short element, constitute a sound structure or device; one or more structures are distributed on the detection apparatus. Preferably, the two or more sound structures give sounds simultaneously and the two sounds resonate. With the resonance, the sound is more crisp and loud. Alternatively, the two sound sources simultaneously emit a frequency or the same sound wave, and the two sounds are superimposed on each other to make the audible sound louder. In some preferred embodiments, the structures making a sound are distributed symmetrically. In some preferred embodiments, there are three structures making a sound, which are distributed evenly at an angle of 120 degrees of the circumference. In some preferred embodiments, three structures or devices making sounds are distributed around a concentric circle.

DETAILED DESCRIPTION

Figure 1:
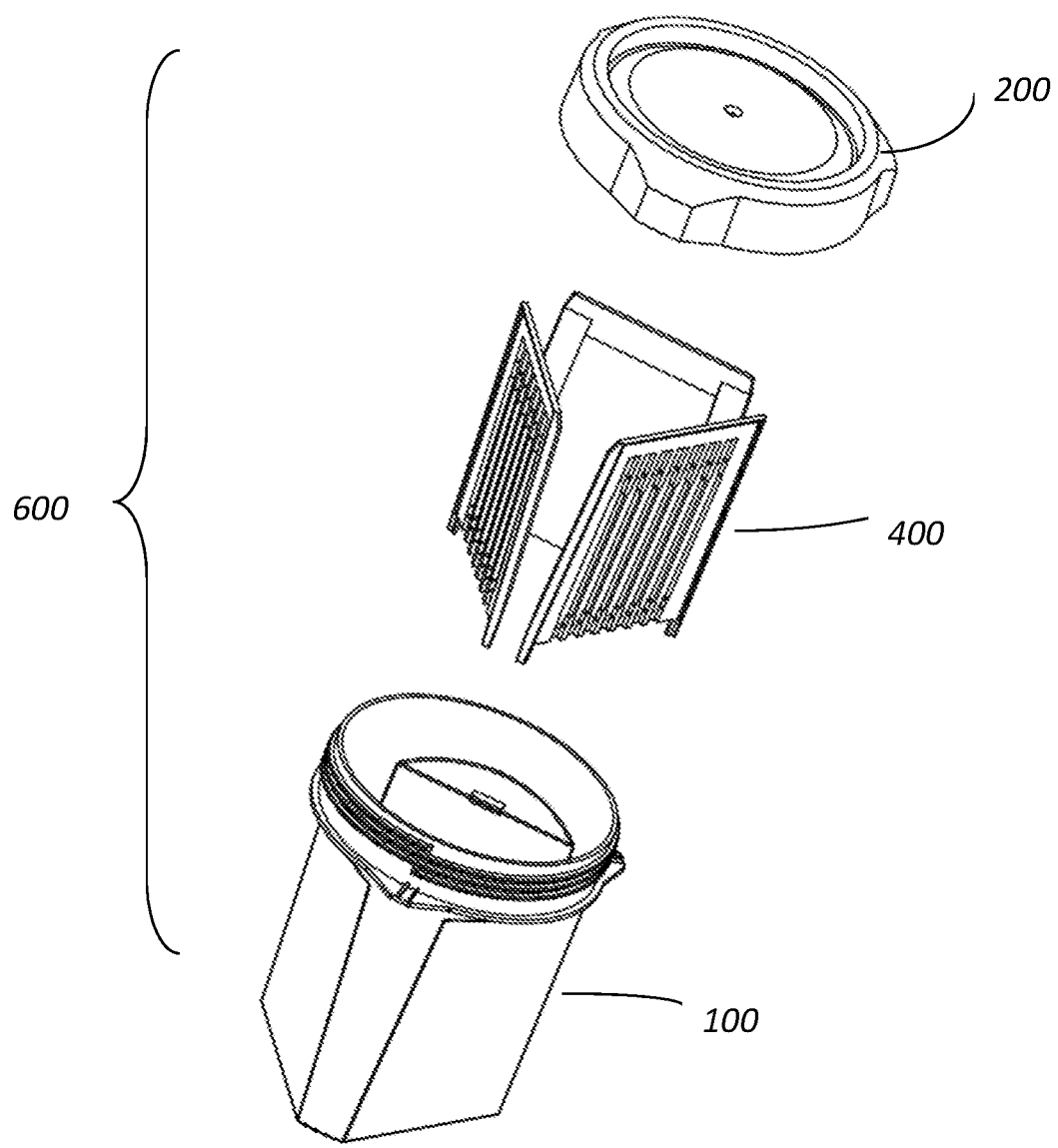
FIG. 1 is a schematic perspective view of a detection apparatus according to a particular embodiment of the present invention.

The structures involved in this invention or the used technical terms are further described below. These descriptions are only to explain how to achieve the ways in this invention through examples, and will not restrict this invention. The scope of this invention is defined and expressed by claims.

Detection

Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of, or the presence or absence of a substance or material. Furthermore, assay also means immunodetection, chemical detection, enzyme detection, nucleic acid detection and etc.

Downstream and Upstream

Downstream and upstream are divided according to the flow direction of liquid, and generally, liquid flows from upstream to downstream regions. The downstream region receives liquid from the upstream region, and also, liquid can flow to the downstream region along the upstream region. Here we often divide the regions according to the flow direction of liquid. For example, on some materials that use capillary force to promote liquid to flow, liquid can flow against the gravity direction, at this time, the upstream and downstream regions are still divided according to the flow direction of liquid.

Gas Flow or Liquid Flow

Gas flow or liquid flow means that liquid or gas can flow from one place to another place. In the flow process, some physical structures may play a role of guidance. Here, liquid or gas can flow due to self action (gravity or pressure), and can also be driven to flow.

Testing Element

Various testing elements can be combined and applied to this invention. The testing element includes a test strip, which can be analyzed in various forms such as immunoassay or chemical test to detect such analyte in samples as drugs or relevant metabolites indicating physical conditions. In some forms, the test strip is a water absorbent material having liquid sample adding (applying) area, reagent area and testing result area. Samples are added to the adding area, and flow to the reagent area under the capillary action. In the reagent area, samples dissolve the reagent and mix with it to detect analyte (if there is analyte in samples). Certainly, the reagent area and the sample adding area can also be the same one area. Some reagents treating liquid samples are disposed in advance in the adding area. And samples with reagents continue to flow to the testing result area. Other reagents are fixed in the testing result area, and these reagents react and combine with analyte (if there is analyte in samples) or the first type of reagent in the reagent area. In the noncompetitive detection form, if there is analyte in samples, signals will be generated; and if not, signals will not be generated. In the competitive detection form, if there is no analyte in samples, signals will be generated; and if not, signals will not be generated. The invention applies to the testing element of various analytic forms.

When the testing element is a test strip, it can be made from water absorbent or non-water absorbent materials. A test strip can use various materials to transmit liquid, and one material can be superposed on another material. For example, a filter paper can be superposed on the nitrocellulose. Or in the test strip, a region that at least contains one material is located behind the other region that at least contains a different material. In such case, the liquid circulates among regions, and they can be superposed on one another or choose not to superpose. Materials on the test strip can be fixed on (for example) the holder or hard surface of the plastic gasket, to enhance the test strip's sustainable power.

In some embodiments where some detected objects are detected through a signal generation system (for example, at least one enzyme reacts specifically with the detected object), at least one substance generating signals can be absorbed on the analyte detecting area of the test strip, just like being absorbed specifically on the materials of the test strip as described above. In addition, substances generating signals in the sample adding area, reagent area and analyte detecting area of the test strip or all over the whole test strip can be pretreated in advance on one or more materials of the test strip, which can be achieved by adding the solution of substances generating signals to the surface of the application area or soaking one or more materials of the test strip in the signal solution, after which dry the test strip. Moreover, the above method can be used to pretreat substances generating signals in the sample adding area, reagent area and analyte detecting area of the test strip or all over the whole test strip in advance on one or more materials of the test strip. Furthermore, the signal substance existing in the sample adding area, reagent area and detecting area of the test strip can be added to one or more surfaces of the test strip materials as the labeling reagent.

Areas of the test strip can be arranged as follows: a complete and necessary test strip can include a sample applying area and a testing area. Generally, liquid first contacts the sample adding area, and then flows to the testing area under the capillary action. Certainly, the test strip can also include the following areas according to the needs: a sample adding area or applying area, or at least a reagent area, and a testing area which includes a testing result area, or at least a control area, or at least an adulteration detecting area and a liquid absorption area. If the detecting area includes a control area, the preferred control area is located behind the analyte detecting area of the testing result area. All these areas or their combinations can be on a single test strip containing a material. Additionally, these areas are made from different materials, and are connected together according to the transmission direction of liquid. For example, liquid can be transmitted directly or indirectly among different areas. In this embodiment, different areas can be connected end to end or superposed mutually along the direction of liquid transmission, or connected through other materials such as connecting medium materials (water absorbent materials such as filter paper, glass fiber or nitrocellulose are preferred). By use of the connecting materials, the liquid can flow on materials that connect each area end to end, materials that connect each area end to end but the liquid does not flow, or materials that each area is overlapped mutually (including but not limited to overlapping from end to end) but the liquid does not flow.

If the test strip contains an adulteration detecting control area, the area can be arranged before or after the result detecting area. When the result detecting area contains a control area, the adulteration control area is preferred to be arranged before the control area. In one embodiment of this invention, the test strip is used for analytical judgment and/or control of adulteration. The adulteration control area can be arranged before or after the control area, and preferably, before the control area.

The nitrocellulose membrane test strip is commonly used, that is, the detecting area includes a nitrocellulose membrane on which specific combination molecule is fixed to display the detecting result; and other test strips such as cellulose acetate membrane or nylon membrane test strips can also be used. The test strips and similar apparatuses with test strips disclosed in the following patents can be applied to the testing elements or detection apparatuses in this invention for analyte detection, such as the detection of the analyte in the sample: U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620 and 6,403,383.

In the specific embodiment of this invention, any forms of testing elements or test strips can be located in one or more card slots of base layer 400 or 500 or slot 501 or slot 403, or in the channel that covers the elements (omission) and the card slots on the base layer. Detailed descriptions on how to arrange the test strip in the detection apparatus in this invention will be given below.

Samples

The detection apparatus provided in the invention can be used to detect samples including biological liquid (such as case liquid or clinical samples). The liquid sample or fluid sample can come from solid or semi-solid samples, including excreta, biological tissues and food samples, and these solid or semi-solid samples can be converted to liquid samples by using any suitable methods such as mixing, crushing, macerating, incubating, dissolving or digesting the solid samples in a suitable solution (such as water, phosphate solution or other buffer solutions) with the enzymolysis. "Biological samples" include samples from animals, plants and food, such as urine, saliva, blood and its components, spinal fluids, vaginal secretion, sperms, excrement, sweat, secreta, tissues, organs, tumors, cultures of tissues and organs, cell cultures and media from human or animals. The preferred biological sample is urine; food samples include food processed substances, final products, meat, cheese, liquor, milk and drinking water; and plant samples include samples from any plants, plant tissues, plant cell cultures and media. "Environmental samples" come from the environment (such as liquid samples coming from lake or other water bodies, sewage samples, soil samples, underground water, sea water and effluent samples), and can also include waste water or other sewage water.

Any analyte can be detected by using this invention and a suitable testing element. Preferably, this invention is used to detect the drug micromolecules in saliva and urine.

Analyte

Examples that can use the analyte related to this invention include some hapten substances, including drugs (such as drug abuse). "Drug abuse" (DOA) means to use drugs (often to paralyze the nerves) for non-medical purposes, which will lead to physical and mental damages, and people who use drugs will be dependent on, addicted to drugs and/or die. Examples of drug abuse include abuse of cocaine, amphetamine AMP (e.g. Black Beauty, white amphetamine tablets, dextroamphetamine, dextroamphetamine tablets, Beans); methylamphetamine MET (crank, meth, crystal, speed); barbiturate BAR (such as Valium, Roche Pharmaceuticals, Nutley, N.J.); sedatives (i.e. sleeping adjuvants); lysergic acid diethylamide (LSD); inhibitors (downers, goofballs, barbs, blue devils, yellow jackets, methaqualone); tricyclic antidepressants (TCA, i.e. imipramine, amitriptyline and doxepin); methylene dioxymetham-phetamine MDMA; phencyclidine (PCP); tetrahydrocannabinol (THC, pot, dope, hash, weed and etc.); opiates (i.e. morphine MOP or opium, cocaine COC, heroin, OXY); antianxiety drugs and sedative hypnotics, the antianxiety drugs are drugs mainly used to relieve anxiety, tension, fear and stabilize emotions, having the function of hypnosis and sedation, including BZO (benzodiazepines), atypical BZ, fused dinitrogen NB23C, benzodiazepines, ligand of BZ receptors, open-loop BZ, diphenylmethane derivatives, piperazine carboxylate, piperidine carboxylate, quinazolinones, thiazines and thiazole derivatives, other heterocyclic, imidazole sedatives/painkillers (such as OXY, MTD), propanediol derivatives—carbamates, aliphatic compounds, anthracene derivatives and etc. The detection apparatus provided in this invention can also be used to detect medicines that are easy to overdose for the medical purpose, such as tricyclic antidepressants (imipramine or analogues) and acetaminophen. These medicines will be resolved into different micromolecular substances after being absorbed by human body, and these micromolecular substances will exist in blood, urine, saliva, sweat and other body fluids or in some of the body fluids.

For example, the analyte detected by this invention includes but not limited to creatinine, bilirubin, nitrite, (non-specific) proteins, hormones (such as human chorionic gonadotropin, progesterone hormone, follicle-stimulating hormone), blood, leucocytes, sugar, heavy metals or toxins, bacterial substances (such as proteins or sugar substances against specific bacteria, such as *Escherichia coli* 0157:H7, *staphylococcus, salmonella, fusobacterium, campylobacter, L. monocytogenes, vibrio* or *Bacillus cereus*) and substances relevant with the physiological features in the urine sample, such as pH and specific gravity. For any other clinical urine chemical analysis, the detection can be made by combining the lateral cross flow detection form and the apparatus provided in this invention.

Detection Apparatus

Figure 2:
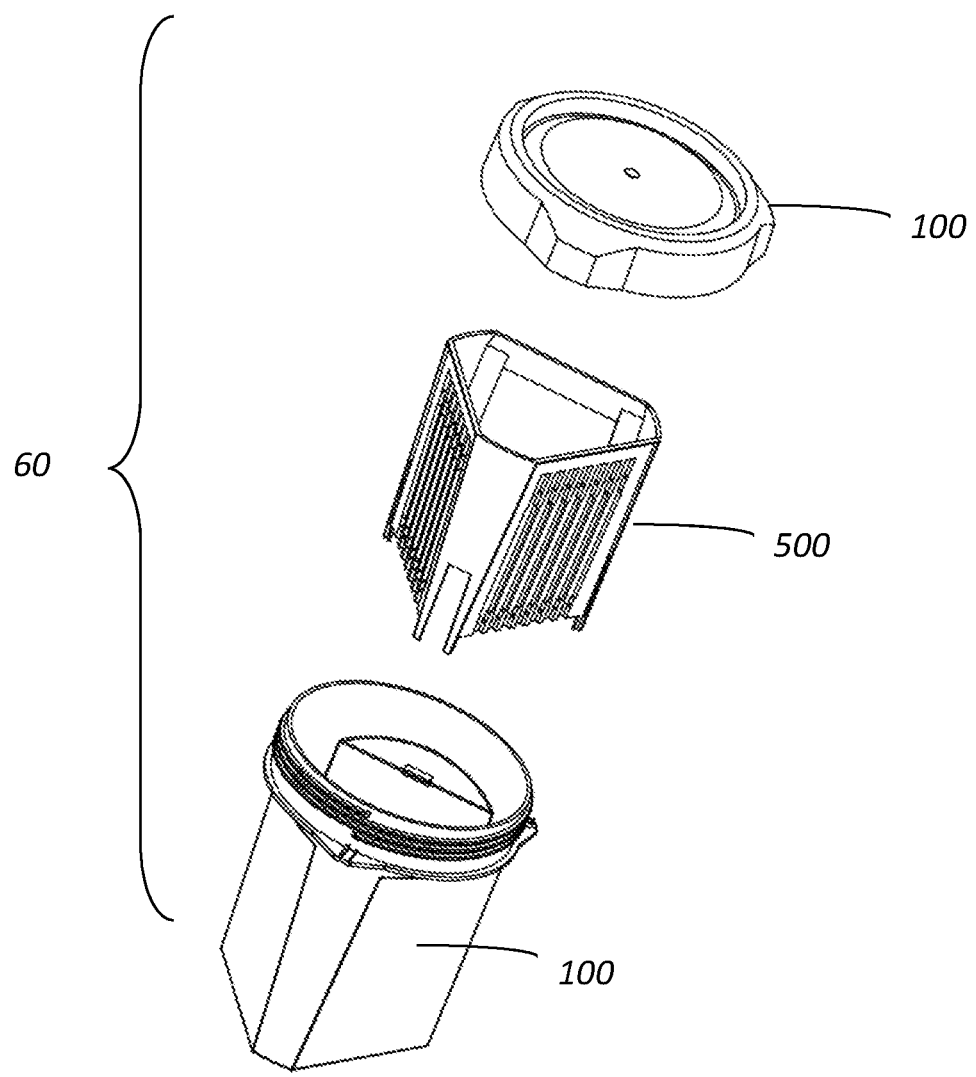
FIG. 2 is a schematic perspective view of a detection apparatus according to another embodiment of the present invention.

The detection apparatus provided in the present invention, 600 as shown in FIG. 1 or as shown in FIG. 2, can be used to detect the presence or absence of, or the quantity of an analyte in a sample by using any technical principle, that is, the qualitative and quantitative detection. The detection apparatus includes a testing element detecting the presence or absence of, or the quantity of the analyte in the sample, and also a device that accommodates the testing element.

Figure 6:
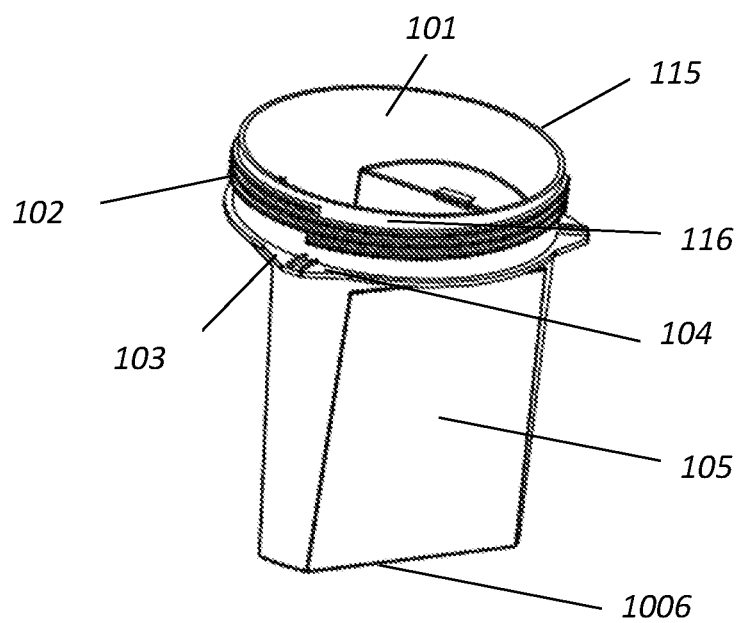
FIG. 6 is a perspective view of a cup body according to a particular embodiment of the present invention.

In a specific embodiment, the detection apparatus includes a collection chamber used to collect and store liquid samples, referring to the collection chamber shown in FIG. 1, the collection chamber 101 in the cup body shown in FIG. 6, or the collection chamber in the cup body shown in FIG. 16-19, which is generally enclosed by side walls and a base, including an opening for leading in liquid samples. "A or an" said in the description of this invention including abstract and claims should be interpreted as at least one, or including one in quantity can not be understood as "unique" or "only one". For example, the detection apparatus includes a prompting device, obviously meaning that the description that the detection apparatus includes two or more prompting devices should also fall into the scope of the claims of this invention and should not be excluded. The detection apparatus can also include a detection chamber 101, and the detection chamber includes a testing element, and the liquid sample in the collection chamber can contact with the testing element in the detection chamber freely or under control; and the chemical reagent on the testing element can test the presence or absence of, or the quantity of analyte in liquid sample. The detection apparatus can also include a cover 200, which is used to cover the opening of the collection chamber. In a specific way, the detection apparatus includes a prompting device, which can prompt if the cover is covered to a specified location, particularly, to a specified location on the collection chamber. On the one hand, when the cover is covered to the specified location of the collection chamber, the prompting device can prompt that the opening of the collection chamber has been sealed by the cover. On the other hand, when the cover is covered to the specified location of the collection chamber, the prompting device can prompt to start to calculate the time needed to wait for reading the test results from the testing element. There are many ways to cover the cover to the collection chamber, such as in the form of thread. For example, the opening of the collection chamber includes the external thread, and the cover includes the internal thread matching with the external thread; after the cover is covered to the collection chamber, the opening is sealed through relative rotation, and moreover, the opening can be sealed by inserting the cover into the opening in the form of piston.

The prompting device provided in this invention can also be applied to other detection apparatuses, particularly, to those apparatuses containing cover and using cover to seal the opening of the collection chamber. These similar apparatuses are described specifically in US patents that have been published such as U.S. Pat. Nos. 7,270,959; 7,300,633; 7,560,272; 7,438,852; 4,976,923; 5,429,804 and 6,726,879. The prompting device disclosed in this invention can be combined to the specific ways of each detection apparatus disclosed in the above patents as one of the specific ways of this invention.

Prompting Device

In a specific way, the prompting device can be arranged on the detection apparatus. The prompting device gives prompts by making a "Pa", "Peng", "Dong", "Dingling", "Pipa" sound or any other suitable sounds. Preferably, such sound can be heard by people.

In some other ways, the opening of the collection chamber is sealed by the cover through relative rotation, a part of the prompting device is located on the cover, and the other part is located on the wall of collection chamber. When the cover is rotated to seal the opening, the part of promoting device on the cover and the other part on the collection chamber generate elastic deformation under the interaction force, and after the force disappears, the parts having elastic deformation collide each other to make a sound to give prompts.

The operating principle of the prompting device provided in this invention is illustrated in combination with FIG. 21A-21G.

The first way of making sounds. The prompting device includes a first element and a second element, which can make a sound by friction between the first element and the second element. Conclusively, the first element has regions that are easier to deform than the second element. For example, since the length of easily deformed regions of the first element 800 is greater than that of the second element, after the two elements are in contact with each other and receive the same force, one element deforms. Or, since the width of easily deformed regions of the first element 800 is greater than that of the second element, after the two elements are in contact with each other and receive the same force, one element deforms. Or, the area of easily deformed regions of the first element 800 is greater than that of the second element, after the two elements are in contact with each other and receive the same force, one element deforms.

For example, the prompting device includes a first element 800 and a second element 900, and generally the first element is located on the cover 200, and the second element 900 is located on the cup body 100. Certainly, the first element can also be located on the cup body 100, and the second element 900 can be located on the cover 200. When the first element and the second element move relative to each other to a certain position, the two elements are in contact with each other (FIG. 21B); as they continue to move, one of the elements such as the first element 800 in FIG. 21C deforms because the length of the first element is greater than that of the second element, the contact point or surface between first elements (one end of 802, first end) is far from the other end 801 (second end) of the first element, while the second element is shorter, and the distance between the two ends 901 and 902 is shorter. When contacting with the first element, almost most of the part between the second element's two ends is in contact with the side face of the first element. So, although the two elements receive the same force, the first element 800 is the one that is easy to deform. As the two elements move further relative to each other, the second end surface 802 of the first element slides from the end surface 902 of the second element, and the first element slightly bends (a type of deformation) due to the interaction force between the two elements, and the end surface 802 of the first element and the end surface 902 of the second element generate friction to let the first element vibrate, thus making a sound. The sound reminds the operator that the cover is rotated to a certain position and there is no need to rotate the cover further. In this embodiment, the material of the first element can be the same as that of the second element, for example, both of them are of plastic material or other materials such as iron sheet and copper sheet. As long as the contact surface between them is relatively rough, large friction will be generated. As they move relative to each other, the change of friction will make one of the elements vibrate and give sounds. Certainly, for better vibration of one element, for example, the first element is of sheet shape such as of sheet materials, it will be easier to vibrate with a certain frequency, and thus making sounds. As said before about the contact point or surface of the two elements, for the first longer element, its contact surface is far from another fixed end (for example, first end 801, which can be fixed on the cover), while the second element (for example, it can be fixed on the cup body) is shorter, and almost it will not deform, thus the first element is easy to deform. Such deformation is generated due to the different length of the two elements, and it has little relation with the material itself. For example, the first element is copper sheet, iron sheet or steel sheet, and the second element is plastic. As long as the two elements are in contact, friction will be generated.

Figures 21A, 21B, 21C:
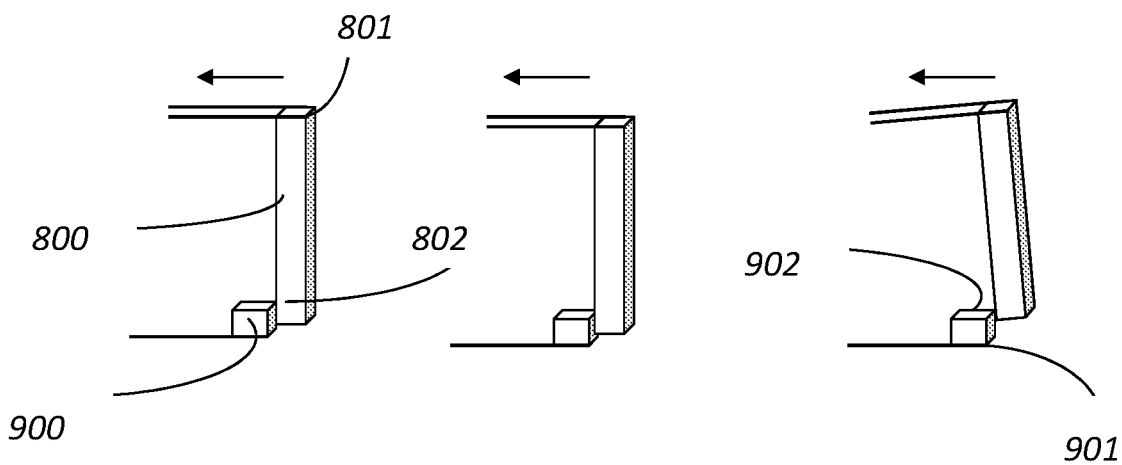
FIG. 21A-FIG. 21G are schematic diagrams of working principle of a structure making a sound in the present invention.
Figures 21D, 21E:
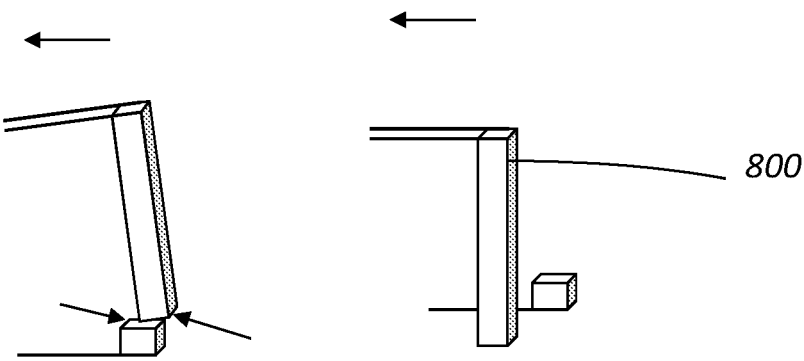

The second way of making sounds. Of course, in some other ways, as the first element and the second element continue to move, the first element slides through the second element to leave away from the second element. Since the first element is deformed (for example, bent or twisted), it is required to restore to its normal initial state and produce vibration to making a sound (FIG. 21E). In this embodiment, the first element can be made of material which is prone to be elastically deformed, for example, "elastic material", and the second element may be made of a "rigid material" which is less prone to deformation. In this way, vibration is likely to occur.

Figures 21F, 21G:
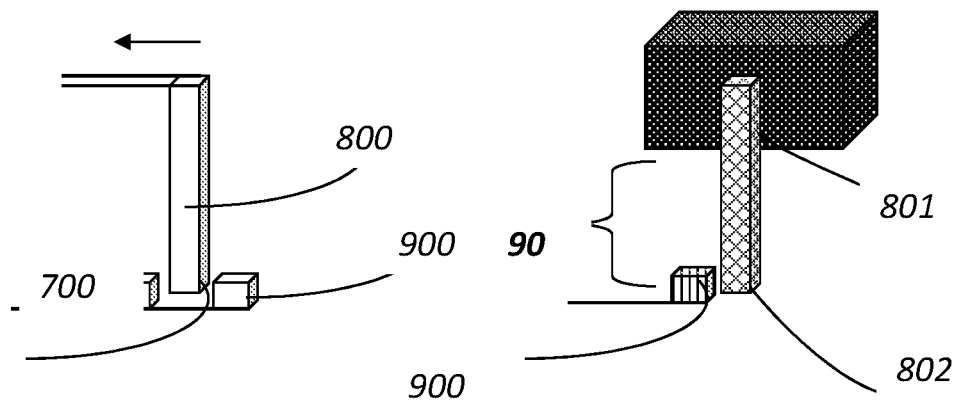
Figure 22:
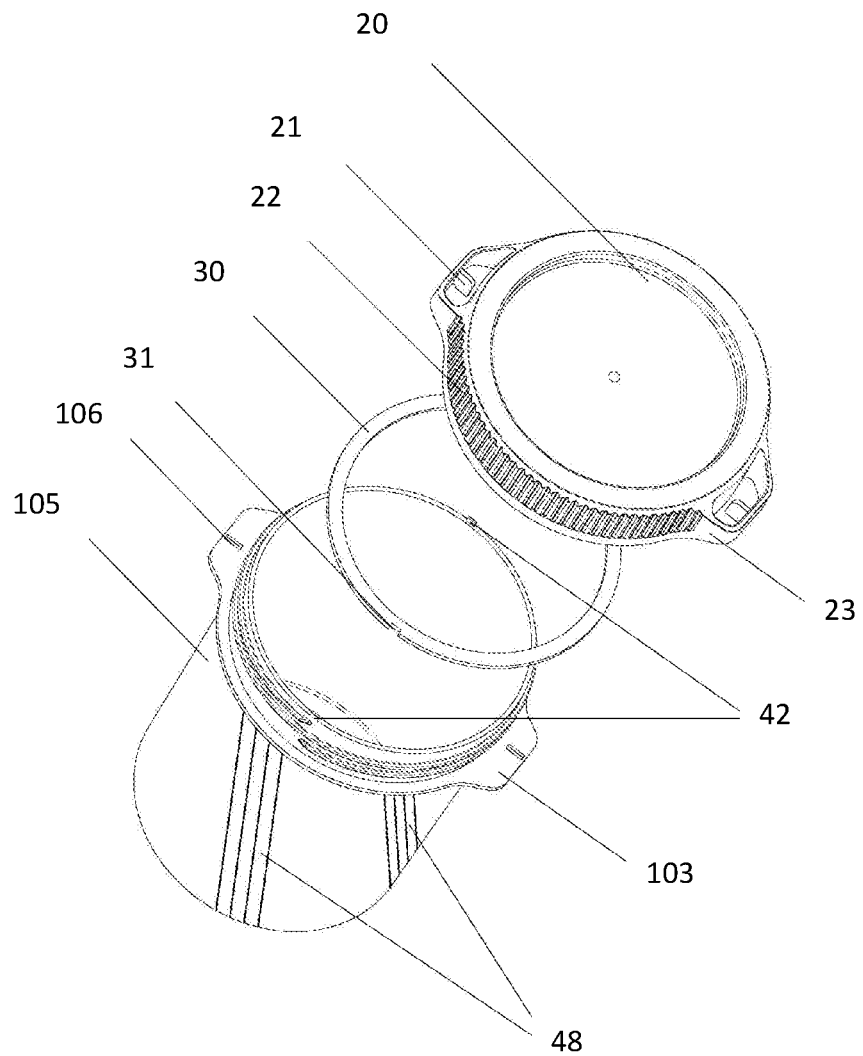
FIG. 22 is an exploded view of a detection apparatus according to another embodiment of the present invention.

The third way of making sounds. Of course, in other specific ways, to make the sound clearer, there are two second elements (second element 900, third element 700), when the first end 802 of the first element passes through the second element 900 and leaves the first element, since the second end 801 of the first element 800 (fixed end, generally connected with the cover) is in the front position and the first end 802 is in the back position due to resistance, when leaving from the first element, both ends of the first element have a trend to return to the same position, the first end 802 moves forward to the position of the second end represented by 801, so that the first end 802 moves forward to collide with the third element to produce a sound. The position of the third element 700, or the distance between the second element 900 and the third element should be less than the distance between the fixed end 801 of the second element and the first end of the first element obstructed. The fixed end of the first element is in the same location as that of the blocked end 801. Since the first end 802 of the first element is blocked by the second element so that the fixed end 801 of the first element and the blocked end 801 of the first element produce a position shift. The position shift is associated with the resistance exerted on the first end, the distance between the fixed end 802 and the blocking end (first end 802), and the length or height of the second element. Generally the greater the distance between the fixed end 802 and the blocking end (first end 802), the greater the position shift, or the greater the resistance, the greater the position shift, or the higher the second element, the greater the resistance and the greater the position shift (FIG. 21G). Thus, when the resistance disappears, the fixed end 801 of the first element and the blocked end 802 of the first element need to return to the same position, so that the first end 802 swings forward quickly to collide with the third element 700 and make a sound.

The above three ways can make a sound, but one, or two or three ways can be chosen to make a sound. Of course, as shown from FIG. 21, regardless of friction, or free vibration, or collision with the third element, it happens within a very short period of time, by this way, it ensures that the sound can be heard, in addition, several kinds of sounds may be made within a very short period of time, and the sound waves have a superposition effect, so the sound is heard more crisply and loudly.

Figure 5:
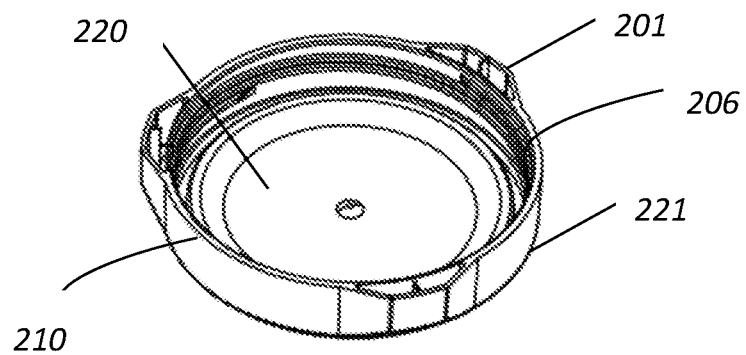
FIG. 5 is a perspective view of a cover according to a particular embodiment of the present invention.
Figure 8:
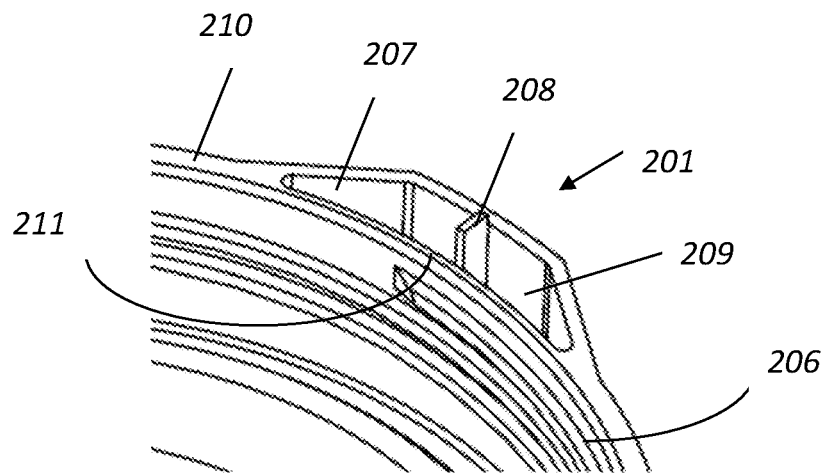
FIG. 8 is a partially enlarged schematic perspective view of a cover according to a particular embodiment of the present invention.
Figure 9:
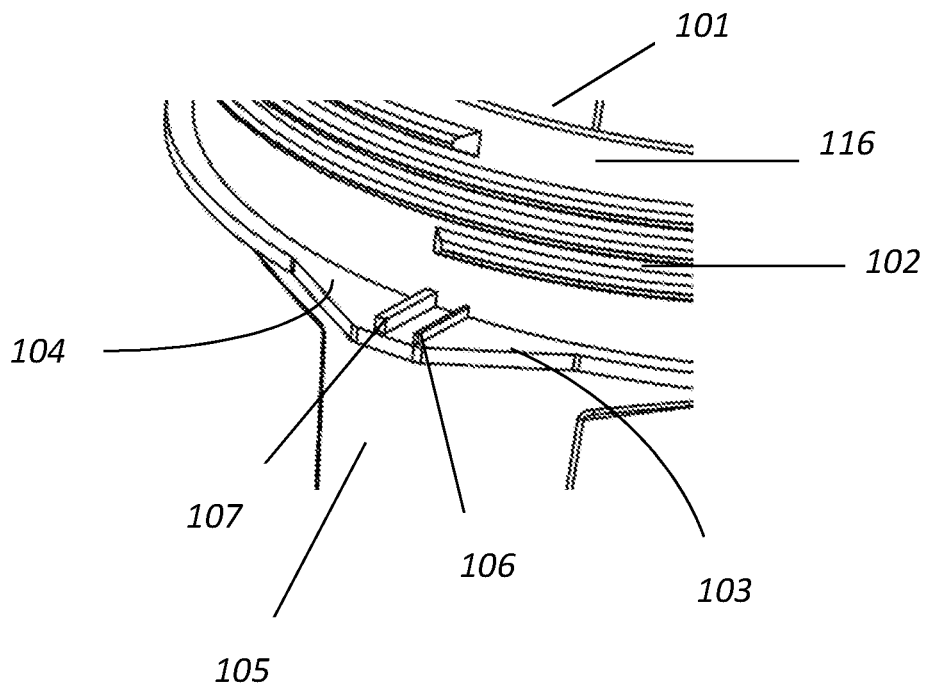
FIG. 9 is a partially enlarged perspective view of a cup body according to a particular embodiment of the present invention.
Figure 10:
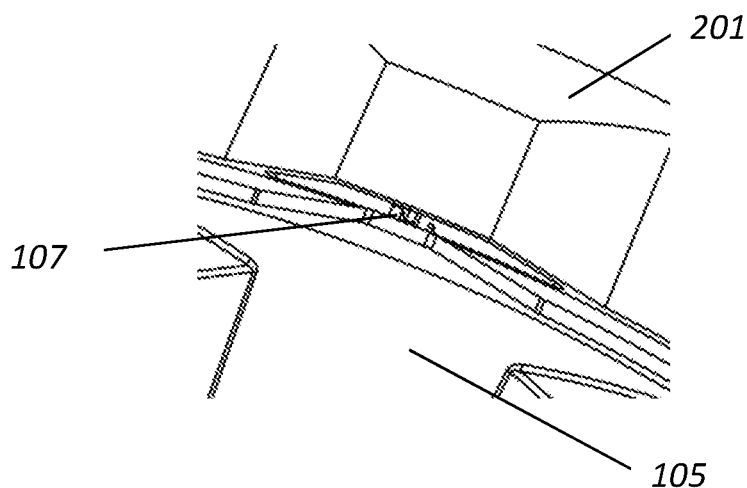
FIG. 10 is a partially enlarged perspective view of a cover and a cup body according to a particular embodiment of the present invention.
Figure 11A:
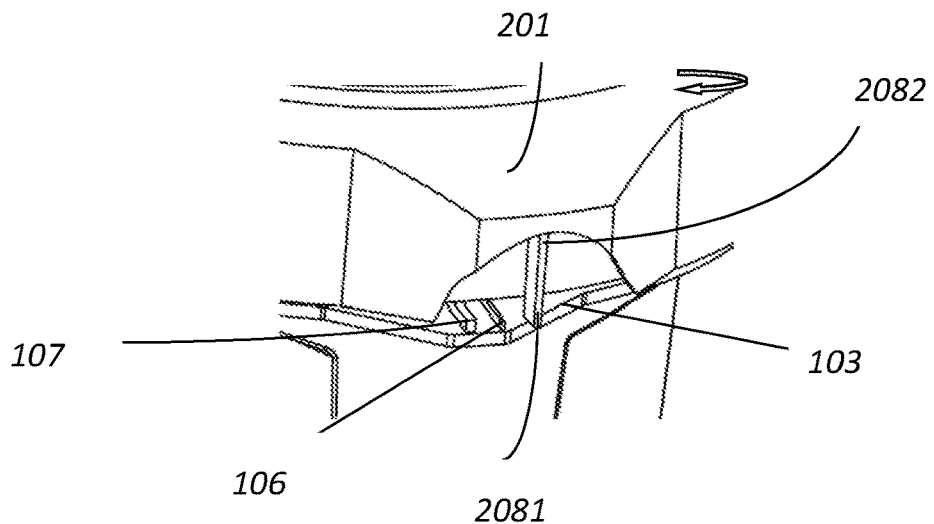
FIG. 11A-FIG. 11C are schematic views of making a sound when a cover moves relative to a cup body according to a particular embodiment of the present invention.
Figure 11B:
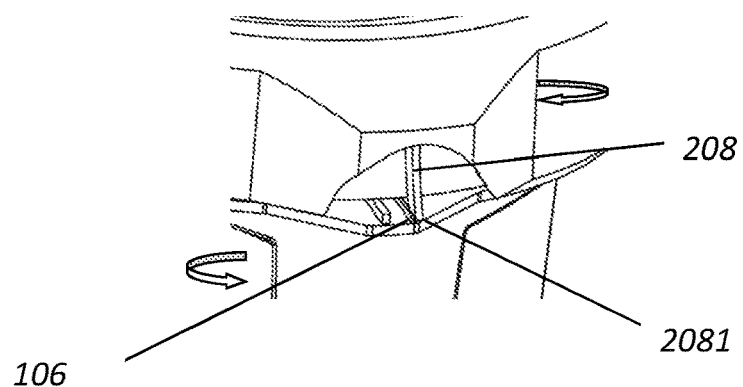
Figure 11C:
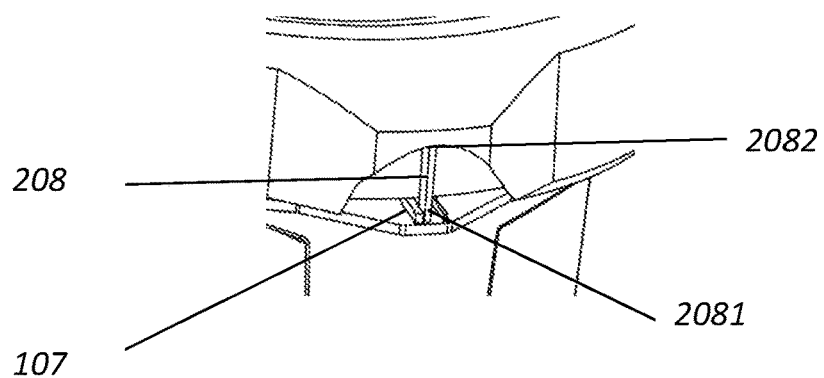

In some preferred ways, referring to figures, how the sound is emitted from detection apparatus is illustrated, for example, FIG. 5, FIG. 8 show the schematic views of the first element located on the cover, FIG. 6, FIG. 9 show the schematic views of the second element on the cup body. FIG. 10 shows the position relationship between the first element on the cover and the second element on the cup body. FIG. 11A-FIG. 11C is a process diagram of making a sound with the coordination of the first element and the second element. Now, it is described in detail with reference to the accompanying drawings.

The first element on the cover is illustrated with reference to FIG. 5 and FIG. 8, for example, first plastic sheet 208 or other easily deformable or not easily deformable material. The cover 200 is generally used to cover the opening of the cup body through the piston type and threaded rotation for covering the cup body. Therefore, usually there is a thread 206 in the cover, and the thread matches with the external thread 102 of the cup body 100, to rotate and seal the opening 115 of the cup body. Thus, the cover is generally surrounded by a cover bottom 220 and a cover edge 221, the cover edge 221 has a certain thickness, with the side 210 of the cover edge. Generally the cover is in a concentric circle shape. The thread 206 is provided on the inner surface of the cover edge 221 in conjunction with the thread 102 of the outer edge of the opening 115 of the cup body 100. The first plastic sheet 208 is arranged at the location of the outer surface of the cover edge 221 (FIG. 5 or FIG. 8), and on the outer surface of the cover is provided with a chamber 207 having an opening. The chamber is enclosed by part of the outer surface 211 of the cover edge and another side wall 209, while the first element, for example, the first plastic sheet 208, is located in the chamber 207, so that the first plastic sheet 208 is parallel to the longitudinal axis of the cover or parallel to the longitudinal axis of the cup body, the first element, for example, the plastic sheet 208 may be of the same material with as the cover or another material, for example, a steel sheet, one end of the sheet may be welded to outside of the cover edge 221, or one end of the first plastic sheet 208 is fixed (called as first fixed end) on the outer edge of the cover. The first plastic sheet 208 and the cover are made by one-time injection molding. One end (second end 2082) of the first plastic sheet is fixed on the outer edge and the other end (first end) 2081 is suspended. The chamber 207 having the first element is not necessary in the present invention but as a priority solution.

For the cup body 100, similar second element can be provided. The second element can be, for example, a second plastic sheet, which is arranged on the outer surface of the cup body (FIG. 6), thus, when the cover is rotated, the first element, for example the first plastic sheet 208, can contact the second element for example second plastic sheet 106 (FIG. 9). In a more preferred embodiment, the second plastic sheet 106 is located on the skirt 103 extending outwardly of the cup body, preferably, the second plastic sheet 106 is perpendicular to the longitudinal axis of the cup body or perpendicular to the face where the outer edge 116 of the cup opening 115 of the cup body 100 is located, actually the second plastic sheet is distributed radially on the skirt 103. In this way, when the cover moves to a certain position, the first plastic sheet with the vertical axis parallel to the cup body has opportunity to contact with the second plastic sheet perpendicular to the longitudinal axis of the cup body from being blocked.

In order to allow the cover 200 to rotate to seal the cup body, a thread is arranged on the face of the outer edge 116 of the opening 115 of the cup body, and the cover rotates with the cup body through the thread, to move downwards along the vertical axis of the cover and cup body, so that the side 210 of the cover edge 221 of the cover 200 is gradually close to the skirt 103 of the cup body 100. The distance between the threads in the cover and the threads outside the cup body allows the first plastic sheet 208 on the cover to be located just before the second plastic sheet 106 when the cover is sealed in the opening of the cup body or just to seal the opening. (FIG. 11A), with the further rotation of the cover and the cup body, the first end 2081 of the first plastic sheet 208 is in contact with the second plastic sheet 106 (FIG. 11B); with the further rotation, the cover drives the second end 2082 of the first plastic sheet to move forwards, but the first end 2081 of the first plastic sheet is blocked by the second plastic sheet 106; with the continuous rotation, the cover drives the second end 2082 of the first plastic sheet to move forwards continuously, at this time, the first end 2081 of the first plastic sheet is still blocked, and the edge 201 of the cover is gradually close to the skirt 103 of the cup body, by this way, a horizontal resistance is generated between the first plastic sheet and the second plastic sheet, at the same time, the cover moves downwards gradually with longitudinal pressure, so that the acting force between the first plastic sheet and the second plastic sheet is gradually increased. With reference to FIG. 21 and the description in FIG. 11, when the cover continues to rotate, the cover continues to move downward, and the first end of the first plastic sheet slides over the surface of the second plastic sheet; because of the presence of longitudinal force between them, the frictional force between the surface of the first end of the first plastic sheet and the surface of the second plastic sheet is increased so that the first plastic sheet vibrates to make a sound during the sliding. Of course, to make the friction more intensive, the surface of the second plastic sheet can be wider and more rough, for example, the width of 0.2 mm, 0.5 mm, 1 mm, 2 mm, 3 mm, 4 mm, so that the end face of the first plastic sheet moves longer on the surface of the second plastic sheet, with a greater frictional force and longer duration, and the vibrating sound can be made continuously.

In addition, based on the above discussion, when the fixed end 2082 of the first plastic sheet moves forward with the cover, the blocked end 2081 is blocked by the second plastic sheet, by this way, the end 2082 fixed on the cover and the plastic sheet before the first end 2082 will be distorted, bent or deformed. Once the resistance disappears (without the blockage of the second plastic sheet 106), the bent end 2082 will move forward quickly, to produce vibration and thus make a sound during the movement.

As a preferred embodiment, a third plastic sheet 107 is provided on the cup body, which is arranged in parallel with the second plastic sheet, with a distance between them. With the setting of the distance, the first end 2081 of the bent first plastic sheet will move forward quickly after leaving the second plastic sheet 106, to hit the third plastic sheet 107. This hitting will make a sound, and the first plastic sheet will produce vibration and make a sound.

For example, as shown in FIG. 11A-11C, the above three ways can be realized simultaneously. Of course, it is also possible to select one of them as an alternative.

In some other ways, the second plastic sheet 106 or the third plastic sheet 107 is protruding upwards from the surface of the skirt 103 of the cup body, to touch the first plastic sheet. In order to prevent the second plastic sheet 208 from exposed outside, a chamber 207 is provided on the cover to receive the first plastic sheet 208, to allow the fix end 2082 of the first plastic sheet 208 to be secured in the chamber and another end 2082 is exposed outside of the chamber. In order to contact the second plastic sheet 106 on the cup body, the other end 2082 of the first plastic sheet is exposed to a certain height (FIG. 8). When the opening of the chamber 207 for receiving the first element is at the same height as the side 210 of the cover edge, the chamber 207 can protect the second plastic sheet. In addition, the second plastic sheet 208 may be hidden, increasing the mystery of the sound and the operator's sensitivity.

Of course, in order to allow the cover to rotate smoothly, before one end 2081 of the first plastic sheet 208 is in contact with the second or third protruding plastic on the surface of skirt 103, the end 2081 of the first plastic sheet 208 is not in contact with the surface of the skirt 103, thereby reducing the friction between one end 2081 of the first plastic sheet 208 and the surface of the skirt 103 and reducing the resistance. In this way, only when rotating to the fixed position or the pre-set position, the end 2081 of the first plastic sheet 208 can be in contact with the second plastic sheet 106, thereby making a sound as described above.

As the principle of the workflow illustrated in FIG. 11, three different sounds are made within a very short period of time such as 0.1 second, 0.5 second, or of second, and they can be superimposed together and transmitted to an operator via the air. With the superposition, the sound is greater, louder and more crisply.

In some preferred embodiments, the second plastic sheet or second plastic element 106 or the third plastic sheet or third plastic element 107 is in contact with the first plastic element or the first plastic sheet 208 at an angle of 90 degrees or any other angle, such as 80 degrees, 70 degrees, 45 degrees, as long as they can contact each other. Of course, the most preferred way is within the angle of 80-90 degrees. Of course, it is preferred that the material of the second plastic sheet or the second plastic element 106 or the third plastic sheet or third plastic element 107 is same as that of the cup body, or may be different, and when the material is the same, it can be easily made by one-time injection molding.

In these embodiments, since the second plastic sheet or the second plastic part 106 or the third plastic sheet or the third plastic element 107 is protruding, with a certain height, while one end 2082 of the first plastic element or the plastic sheet 208 is fixed on the cover, while the other end 2081 is suspended, and the length between the other end 2081 and the fixed end 2082 will decide the degree of bending and deformation of the first plastic element, and if the distance between them is longer, the deformation may easily occur, and a small force may induce deformation; on the country, the shorter, the more difficult for deformation and deformation needs a large force. Of course, this distance, i.e. the length or distance between the other end 2081 and the fixed end 2082, is greater than the height of the second plastic sheet or second plastic element 106 or the third plastic sheet or third plastic element 107 protruding on the skirt. By this way, it is easy to make a sound when the material of the first element or second plastic element is the same as that of the second or third element or the second or third plastic element.

Alternatively, in some alternative embodiments, when the material of the first element or second plastic element is not the same as that of the second or third element or the second or third plastic element, the first element may be of an elastomeric material such as a thin plastic sheet, a thin metal sheet, and the second element is of a rigid material, such as a hard plastic, or a hard metal strip, so that the elastic element is in contact with the rigid second element. As described aforesaid, the first element is prone to deformation and make a sound.

In some preferred embodiments, three identical parts of the sound structure (FIG. 5) are included on the cover, including, for example, three first element structures, and three corresponding identical parts of the sound structure are included on the cup body, for example, the corresponding second element and/or third element. In this way, when the cover is covered to the cup body, the three structures can make sound simultaneously and superimpose together, making the sound more crisply and louder. In some preferred embodiments, three first elements on the cover are distributed in an equally rounded circumference, with an angle of 120 distributed over the cover edge. Accordingly, the second blocking element on the cup body is distributed correspondingly so that they can make a sound simultaneously.

Figure 7:
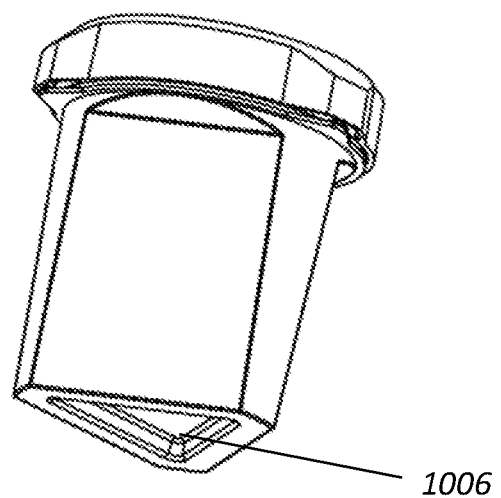
FIG. 7 is an assembled schematic perspective view of a detection apparatus shown in FIG. 1 or FIG. 2 in the present invention.

In still some preferred embodiments, there are three (FIG. 5) or two chambers 207 (FIG. 23) protruding outwardly from the cover edge 221, when an operator holds the cover for rotating, it is easy to hold the cover and rotate by applying force. These protruding structures can facilitate to apply force with hands and operators can feel comfortable. Correspondingly, the three-dimensional shape of the cup body 100 is triangular (FIG. 1, FIG. 2, FIG. 7), and the triangular cup body is easy to grasp, so that it is easier to grasp than the cylindrical cup body, in addition, it is easy to apply force without sliding from hands when rotating the cover.

Collection Chamber and Detection Chamber

Figure 17:
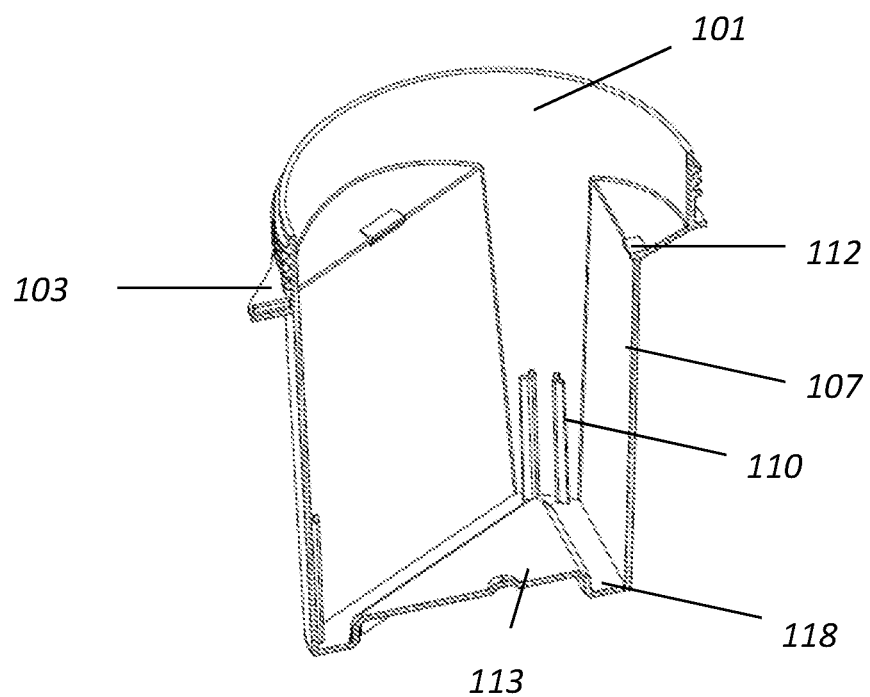
FIG. 17 is a partial cross-sectional view of a urine cup as shown in FIG. 16 in the present invention.
Figure 18:
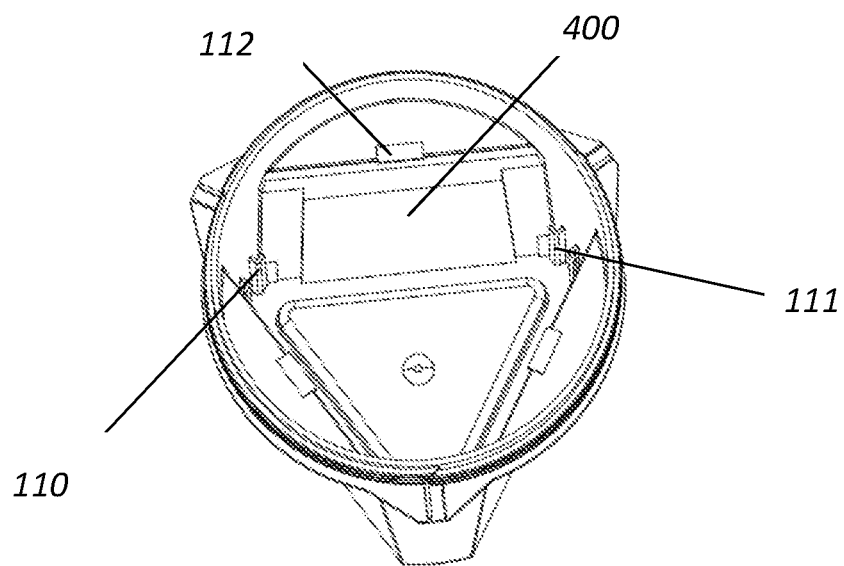
FIG. 18 is a schematic view of a urine cup and a base layer after assembly according to another embodiment of the present invention.
Figure 19:
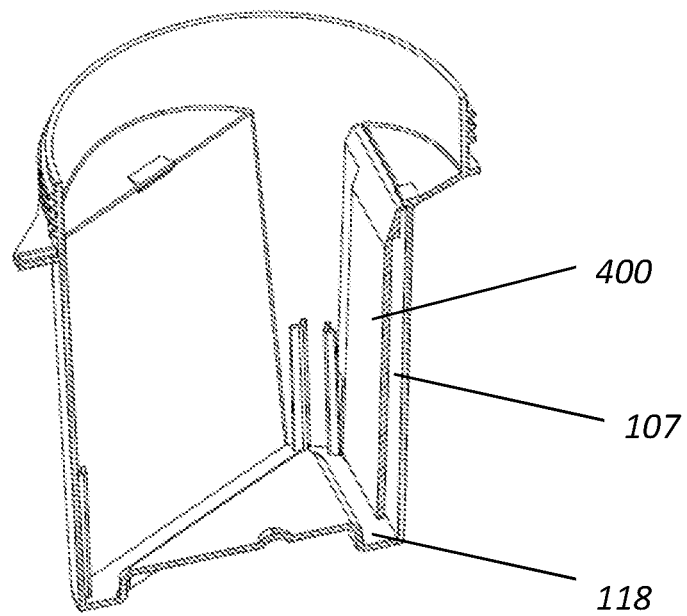
FIG. 19 is a partial cross-sectional view of a urine cup and a base layer after assembly as shown in FIG. 18 in the present invention.

Referring to the structure of a cup body shown in FIG. 1-3, 6, 16-19, the detection apparatus disclosed in the invention further includes a collection chamber for collecting liquid samples, alternatively, the collection chamber can further include a test strip for detecting the presence or absence of, or the quantity of analyte in liquid sample. In the detection apparatus shown in FIG. 1-2, FIG. 6, the collection chamber is located in the cup body 100, and the cup body includes an opening 115, side walls 105 and cup bottom 1006, which enclose the collection chamber 101. The liquid sample enters into the collection chamber 101 through the opening 115, and after the liquid sample is collected, cover the cover 200 to seal the cup body. In some preferred ways, the cup body includes the outer edge 116 of a cup opening 115, on which there is an external thread 102 matching the cover. At the same time, under the thread on the cup opening there is a skirt 103, which can continuously surround the cup body, or extrude at some positions and thus be discontinuous. The skirt 103 extends outwards from the surface of the cup body, on the extended surface there is a second element such as the second blocking element, such as the second plastic element 106 for blocking the first element such as the first plastic element 208 on the cover. As described above, due to the blocking function, the first element deforms, distorts, bends, or the second blocking element rubs against the first element, or there is a third element, the third plastic element 107 collides with the first element, thus making sounds. The shape of the cup body, such as its cross section, can be cylinder, cuboid or cube. But in order to let the cover easily cover and seal the opening of the cup body, the outer edge 116 with threads on the cup body should be round, and the main body of the cup body can be of other shapes. In some preferred ways, the cross section of the cup body is triangular, such as equilateral triangle, referring to the structure shown in FIG. 16-19. As described above, when rotating the cover, with the triangular structure, the operator will be easier to hold it and not to slide. Referring to the structure shown in FIG. 16-17, the collection chamber 101 is triangular, and forms three main support surfaces 107, by which the cup body is enclosed. On each support surface there can be the base layer 400 with card slots or the base layer 500 connected together by three base layers (FIG. 16-FIG. 17) provided in the invention. In some preferred ways, in order to easily install the base layer on the three support surfaces, on these support surfaces the locking structure is provided, and the locking structure can include a locking card 112 and locking anchors 110 and 111. The locking card 112 is arranged in the middle of the position near to the opening 115 on a support surface 107, and the two locking anchors 110 and 111 are respectively arranged at the two sides of the support surface 107 near to the bottom 1006 of the cup body 100 (FIG. 17). In this way, the base layer, referring to the structure shown in 400, after being inserted into the locking structure limited by three points, can be maintained on the support surface 107 and will not easy to fall off (FIG. 18 and FIG. 19).

In some preferred ways, the triangle region 113 extruding upwards on the bottom of the cup body and the three support surfaces form a collecting tank 118 for easily collecting the liquid sample, and making it easier for the test strip on the base layer to absorb the liquid sample. In this way, even if there is little liquid sample, the detection can also be completed (FIG. 17).

Figure 23:
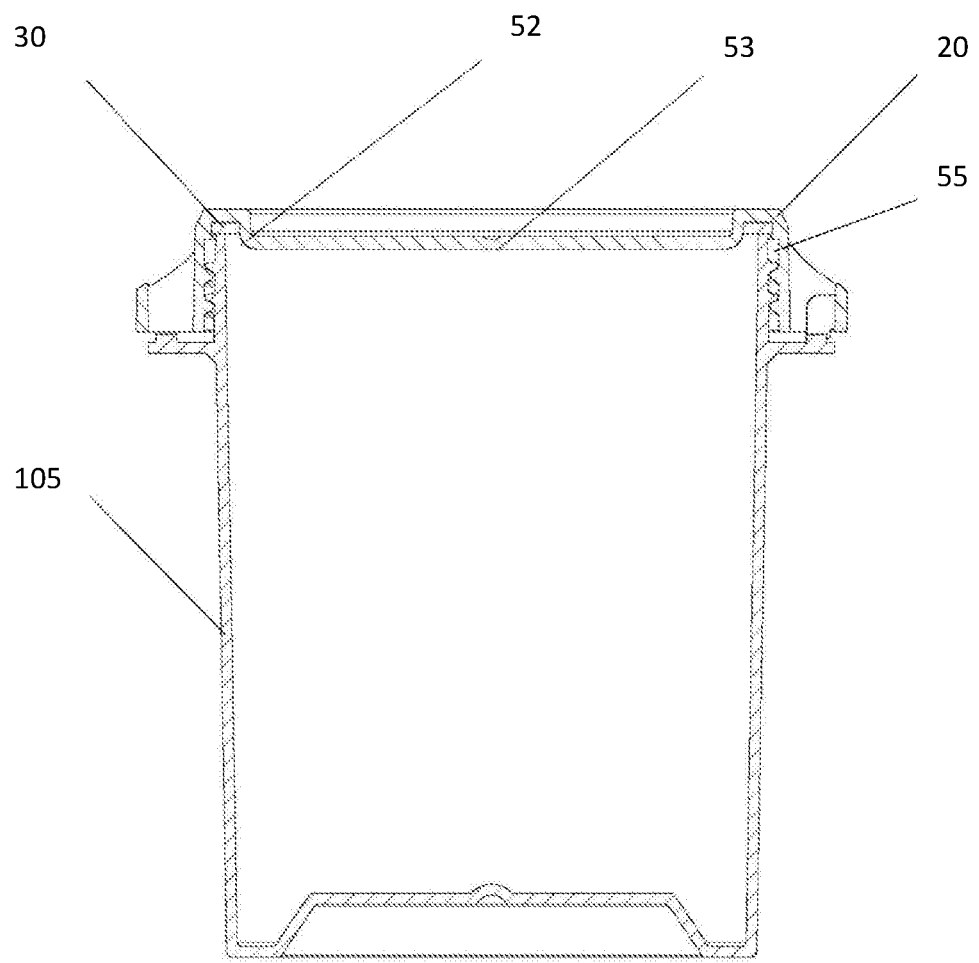
FIG. 23 is a cross-section schematic diagram of a detection apparatus as shown in FIG. 22.
Figure 24:
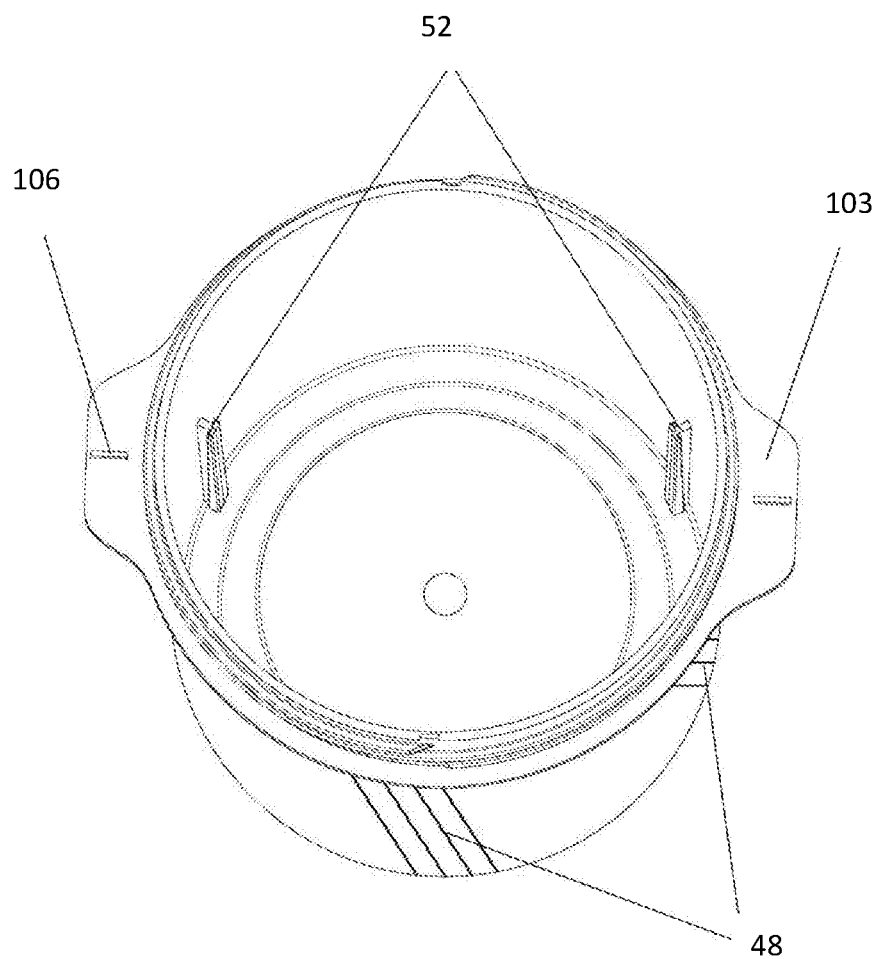
FIG. 24 is a perspective view of a cup body as shown in FIG. 22.

In some other ways, the invention provides some other embodiments, referring to FIG. 23-25, for example, FIG. 23 shows the schematic view of a detecting barrel, that is a detection apparatus, including the cover 20 and the cup body, wherein the cup body includes side walls 105, and the cover 20 contains the internal thread on the inner wall of the side face, the outer wall of the opening of the cup body contains the external thread, and there is a rotating and force application part 22 on the outer wall of the side face of the cover 20.

As shown in FIG. 24, when rotating the cover, a stopper gasket 30 is provided between the cover 20 and the cup body 55 which can prevent the detecting liquid from entering the thread gap 55 from the barrel. The radial width of the stopper gasket 30 is greater than the barrel wall thickness of the opening of the cup body 2. Referring to FIG. 23, FIG. 25, on the cup body there is a positioning part 103 or a skirt region 103, on the skirt region 103 there is a second plastic element 106, and on the cover 20 there is a coinciding part 23 corresponding to the skirt region 103. The coinciding part 23 is of hollow structure, and in the hollow cavity there is a first plastic element 21. The shape and size of the skirt region 103 is the same as or close to that of the coinciding part 23. There is a fixed matching portion between the opening of the cup body and the stopper gasket 30, including a convex piece 42 on the edge of the opening of the cup body and a concave port 31 on the said stopper gasket 30. The convex piece 42 is located on or close to the outer side of the edge of the opening of the cup body, and the concave port 31 is located on or close to the outer ring wall side of the stopper gasket 30. The cup body is cylinder-shaped, and there is a non-slip holding portion 48 on the outer wall of the cup body, a fixed cord 51 for fixing the test strip plug-in card in the collection chamber restricted by the inner wall of the said cup body. The non-slip holding portion 48 is the oblique stripes on the outer wall of the cup body for preventing horizontal and vertical slipping.

Base Layer with Slots

Figure 14:
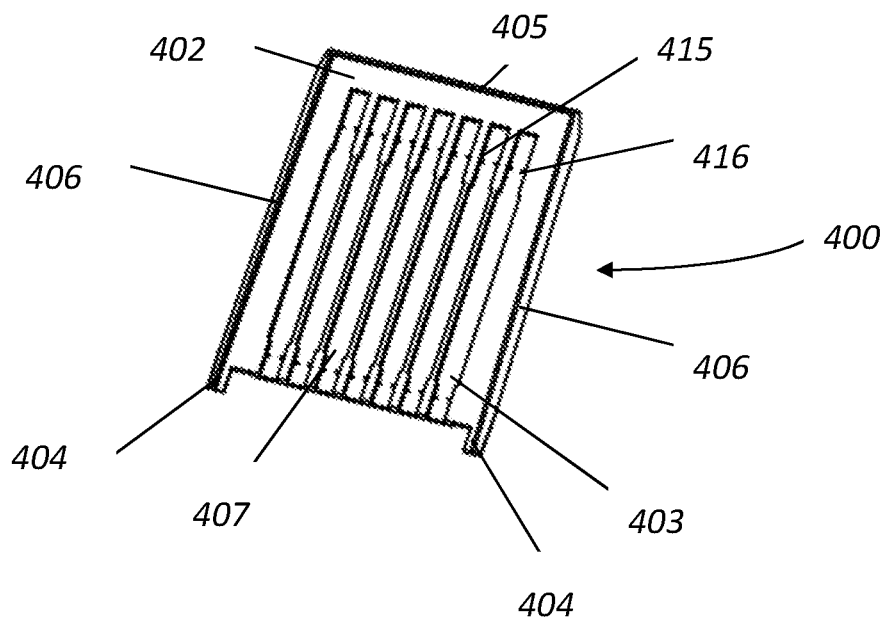
FIG. 14 is a schematic perspective view of a base layer for carrying the testing element according to another embodiment of the present invention (front view).
Figure 15:
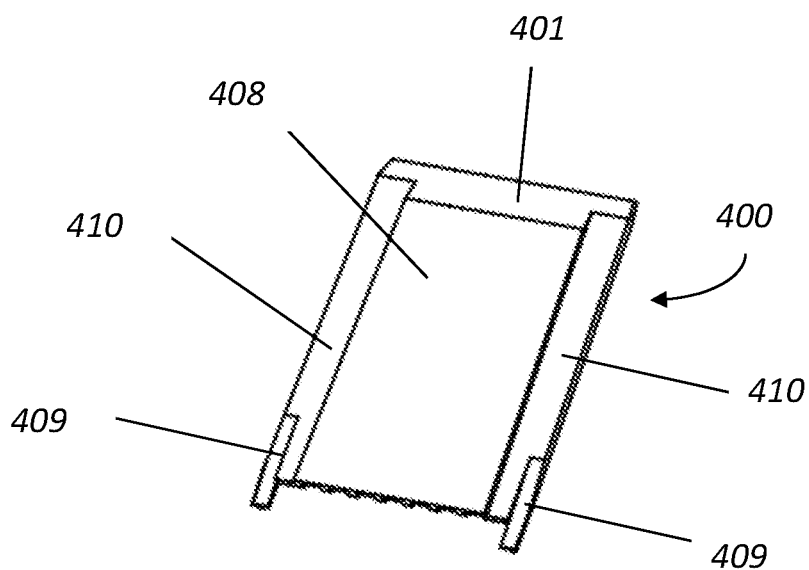
FIG. 15 is a perspective view of a base layer for carrying a testing element according to another embodiment of the present invention (back view).
Figure 16:
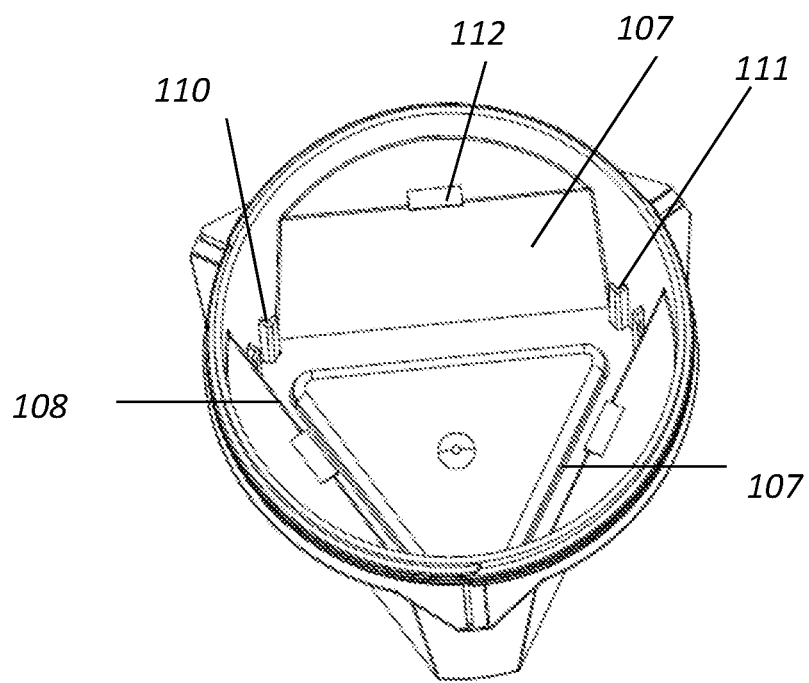
FIG. 16 is a schematic view of a urine cup according to another embodiment of the present invention.

As the collection chamber disclosed above, the test strip can be arranged in the chamber individually, and it can also be put in the base layer with card slots, thus detecting various analytes in a liquid sample. Referring to the base layer 400 shown in FIG. 14-15, the base layer is provided with several card slots 403. The width of the card slot is the same as that of the test strip or the card slot is slightly wider and shorter than the test strip. On each card slot there are two-position fixing knobs 415, 416 for fixing the test strip in the card slot 403. In addition, the base layer further includes two supporting legs 404, respectively located on the two sides of the base layer, and the surface having card slots 403 is slightly lower than the base layer surface, which seems like completely sinking into the base layer surface. Thus, the extruded fencing structures 405 and 406 are formed on one end and two sides of the base layer, the two fencing structures 406 are parallel, and they intersect the other fencing structure 405. By doing so, a covering layer can be covered on the depressed surface to seal the card slots when the test strip is placed in the card slot, thus forming a channel with one end sealed and the other end opened. The said test strip is just located in the channel, and part of the sample applying area of the test strip is exposed, the length of the exposed part is equivalent to that of the two supporting legs.

The back of the base layer is not flat and smooth, which consists of several surfaces with different height. On the upper part of the base layer there is a slope 401, making the cross section of the base layer thinner, and letting the clamping lock 112 easily lock the upper part of the base layer. In addition, there is depressed guide groove 409 at the back of the two supporting legs 404 and 404, through which it is easy to lead in the guide rail formed by locking anchors 110 and 111 on the cup body. Actually, the two guide grooves 409 have a particular structure, this is because in the actual production of the cup body, the distance between the two locking anchors 110 and 111 and the support surface has tolerance, that is, sometimes the distance is longer and sometimes is shorter. When the distance is longer, it is easy to insert into the guide groove formed by the two supporting legs on the base layer, but it is not easy to fix the base layer on the support surface; and when the distance is shorter, it is very difficult to insert. Thus, we can change the depth of the guide groove on the base layer to let the base layer closely cooperate with the guide rail formed by the two locking anchors 110 and 111. When the distance is longer, make the guide groove side shallower; and when it is shorter, make the guide groove side deeper.

Figure 12:
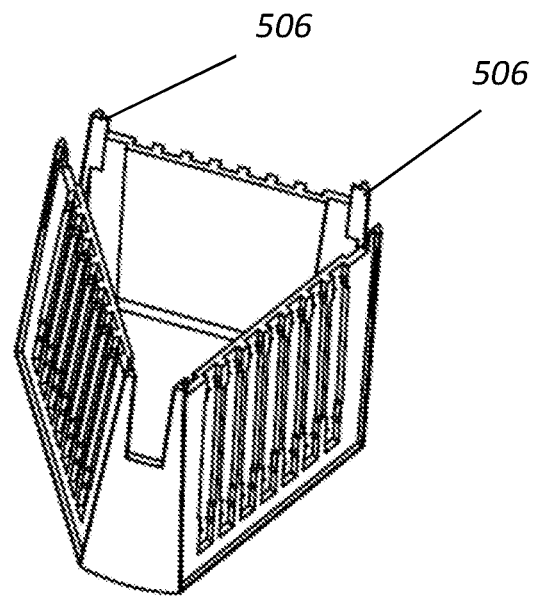
FIG. 12 is a perspective view of a base layer for carrying a testing element according to a particular embodiment of the present invention.
Figure 13:
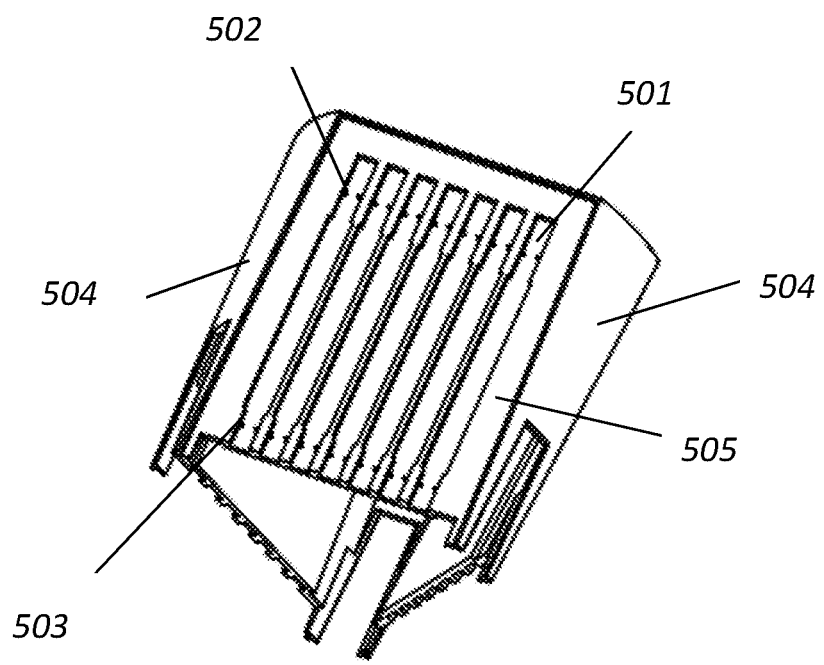
FIG. 13 is a perspective view of a base layer as shown in FIG. 12 in the present invention.

In some other ways, the structure of the base layer can be similar to that of the base layer 400 (FIG. 12 and FIG. 13). On the base layer 500 there are card slots 501, and two supporting legs 506 distributed at the bottom of the base layer. The front and back of each base layer is designed the same as a single base layer 400.

Figure 3:
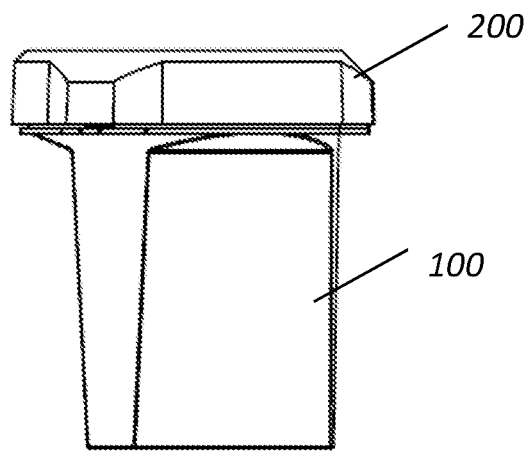
FIG. 3 is an assembled front view of a detection apparatus shown in FIG. 1 or FIG. 2.
Figure 4:
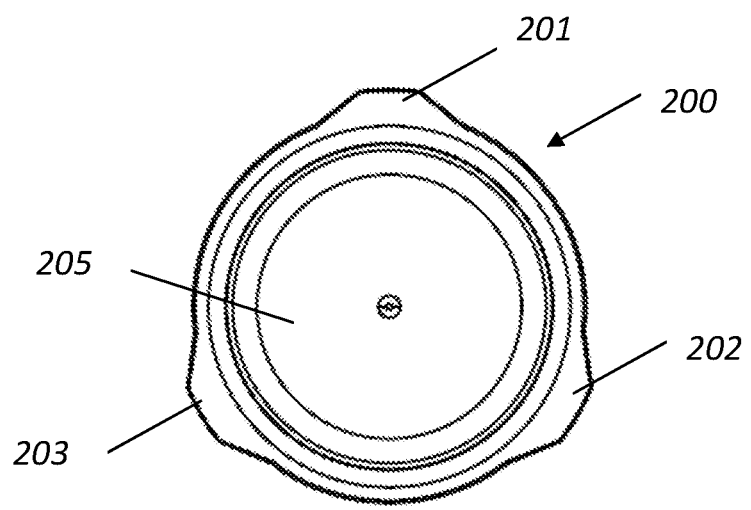
FIG. 4 is a top view of a cover according to a particular embodiment of the present invention.
Figure 20:
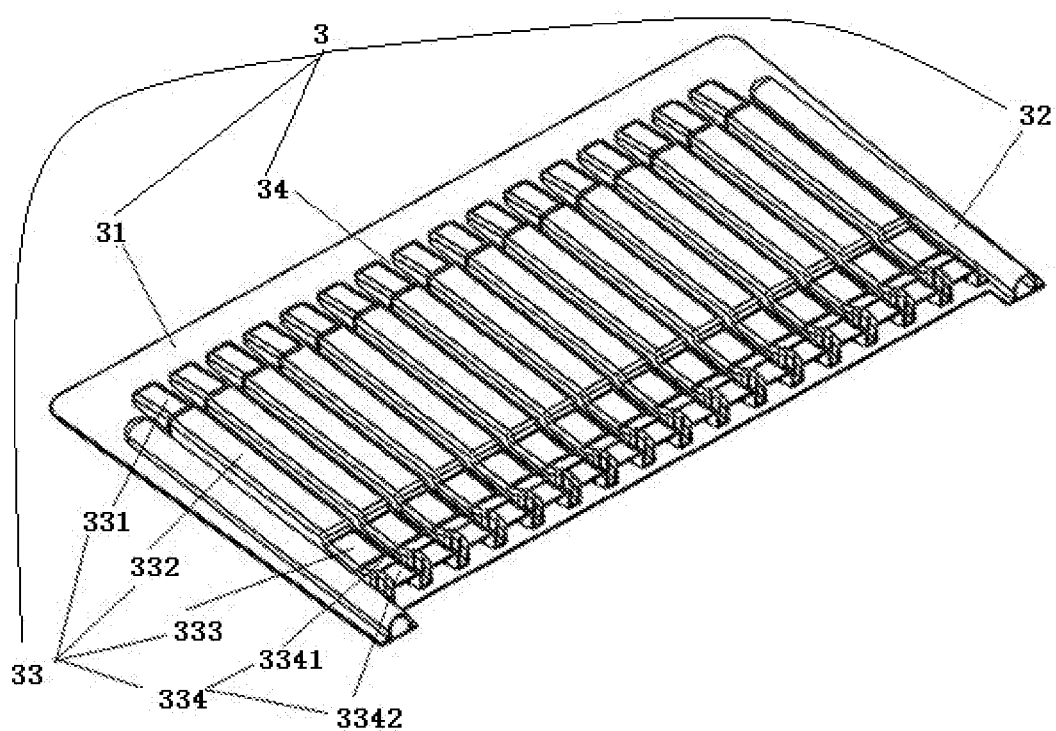
FIG. 20 is a schematic perspective view of a base layer for carrying the testing element according to another embodiment of the present invention.

In some other ways, the structure of the base layer can be that of the base layer shown in FIG. 20. Referring to FIG. 3, the base layer 3 includes an inserting body 31, a fixing portion 32 arranged on the left and right ends of the body 31 for fixing the body 31 on the fixing part 13, more than one test strip slots 33 arranged between fixing portions 32, and a liquid leaking portion 34 arranged between test strip slots 33. The test strip slot 33 includes a clamping portion 331, an observation portion 332 arranged under the clamping portion 331 for observing the test strip, an extrusion portion 333 arranged under the observation portion 332 for extruding the test strip, and a detecting portion 334 arranged under the extrusion portion 333 for further fixing the test strip and contacting the detecting liquid. In this scheme, the base layer 3 is divided into four portions. The fixing portion can be used to fix the whole apparatus, and to stably fix the whole card inserting device in the detecting liquid. Several test strip slots provided here can be used by the tester to test the same one cup of detecting liquid at the same time, thus avoiding repeated pollution or waste of detecting liquid. When the card body is fixed in the detection apparatus and the detecting liquid is added, siphonage phenomenon will not occur due to the arrangement of a liquid leaking portion, thus avoiding the situation that the test strip contacts the detecting liquid too often or the detecting liquid is not detected according to the detecting positions designated by the test strip and leading to an inaccurate detecting result. Additionally, the test strip inserting card provided in this scheme can be made easily by injection molding or pressing molding, with a low cost and a good detecting effect. The fixing portion 32 is set as a hollow structure, for connecting with the fixing part 313 to fix the inserting card on the fixing part 313, thus the test strip can be used to stably detect the detecting liquid in the barrel, avoiding shaking and increasing the precision of detecting effect. The observation portion 332 is wider than the clamping portion 331, the extrusion portion 333 is lower than the observation portion 332 or the clamping portion 331, and the height of the extrusion portion 333 ranges from 0.8 mm to 1.5 mm. The height and width setting of the observation portion is to more conveniently observe the detecting situations of the test strip, and since the inner space of the observation portion is bigger than that of the liquid leaking portion, the probability of occurrence of siphonage is reduced, and the accuracy of detection is increased. On the one hand, the height setting of the extrusion portion is to better clamp the test strip and prevent its displacement, and on the other hand, it is to prevent the detecting liquid from flowing into the observation portion from the extrusion portion and polluting the test strip on the observation portion, and to let the detecting liquid be detected only by the test strip on the detecting portion, so as to improve the accuracy of detection. The detecting portion 334 includes a rising portion 3341 connecting the extrusion portion 333, and a testing portion 3342 connecting the rising portion 3341 for contacting the detecting liquid. The testing portion 3342 is as high as or higher than the extrusion portion 333. The rising portion is only a transition for connecting the testing portion and the extrusion portion, to provide a better liquid level contact area for the detecting positions of the test strip, and to improve the accuracy of detection.

Detection Method

The present invention provides a method for detecting analyte in a sample, including providing a detection apparatus, including: a collection chamber including an opening for collecting a liquid sample, a testing element for testing the analyte in liquid sample; and a cover for covering the opening of the collection chamber; covering the lid to the opening of the collection chamber, so that one prompting device on the detection apparatus can prompt if the cover is covered to the specified location. In one way, the prompting device gives prompts by making a sound. In another way, once you hear the prompting device to give a prompt, stop covering the cover to the opening of the collection chamber. In a specific way, the cover closes the opening of the collection chamber by rotating; and when hearing prompt given by the prompting device, you can stop rotating the cover. In addition, in a way, once you hear a prompt given by the prompting device, start calculating the time to wait for the test results from testing element. In another way, once you hear a prompt given by the prompting device, start calculating the time to wait for the test results from testing element, and stop rotating the cover.

Example 1

Referring to FIG. 1, a detection apparatus of the present invention provides a plastic cup body 100, a cover 200 and three separate base layers 400, and a plurality of card slots of the same structure are provided on the rigid base layer. Each reagent strip provided can be used to detect analytes in the urine, such as amphetamine, cocaine, methamphetamine, opiates, THC, and phencyclidine. Using gold particles as a marker substance, these analytes are detected by competitive methods, then a layer of transparent sticker is covered on the depressed face 402 of the base layer with the same size of the base layer, to form a detection apparatus. A first element is provided on the edge of the cover as the plastic sheet element, with the length of 5 mm, one end of which is fixed to the wall of the chamber and another end is exposed about 2 mm out of the chamber. On the edges of the cup lid, a first plastic sheet is arranged at every 120°. On the skirt of the cup body, two plastic sheets are provided, with the height of 2 mm, and the distance between two plastic sheets is 2 mm, the length is 7 mm. The skirt is 15 mm from the cup opening. A threaded structure is arranged on the outer edge of the cup opening, and the thread engaged with the cup body is also arranged in the inner surface of the outer edge of the cover.

Fifty negative samples are mixed with mixtures of drug abuse, including amphetamines, cocaine, methamphetamine, opiates, THC and phenylcyclohexane, in addition, 50 negative samples are provided.

When testing, these urine samples are poured into the cup, and the cover is covered to the cup body; when a "crackling" sound is heard, stop rotating and wait for the end of the test. Then a real leak test is performed for the covered detection apparatus, and all detection apparatuses are found to keep sealed without leakage of samples.

The invention shown and described herein may be implemented in the absence of any elements, limitations specifically disclosed herein. The terms and expressions used herein are for illustration rather than limitation, which do not exclude any equivalents of the features and portions described herein in the use of these terms and expressions, in addition, it should be understood that various modifications are feasible within the scope of the present invention. It is therefore to be understood that, although the invention has been particularly disclosed by various embodiments and alternative features, modifications and variations of the concepts described herein may be employed by those of skilled in the art, and such modifications and variations will fall into the scope of protection of the present invention as defined by the appended claims.

The contents of the articles, patents, patent applications, and all other documents and electronic information available or documented herein are incorporated herein by reference in their entirety, as if each individual publication is specifically and individually indicated for reference. The applicant reserves the right to incorporate any and all materials and information from any such article, patent, patent application or other document into this application.

What is claimed is:

1. An apparatus for detecting the presence or absence of an analyte in a liquid sample, comprising:
   a collection chamber, comprising an opening with an outer surface for collecting a liquid sample, and the outer surface having a thread thereon;
   a cover for covering the opening of the collection chamber, wherein the cover comprises a cover edge with an outer surface and inner surface, and the inner surface of the cover having a thread thereon in conjunction with the thread of the outer edge of the opening; and
   a cup body comprising the collection chamber, the cup body having an outer edge;
   wherein the apparatus further comprises a prompting device for prompting if the cover is covered to a specified location, and the prompting device comprises a first element, a second element, and a third element, wherein the first element is elastic, and the second element and the third element are non-elastic;
   wherein the first element, with a first end and a second end, is located in a chamber, wherein the chamber comprises an opening, and the chamber, protruding outwardly from the outer surface of the cover edge, is located on the outer surface of the edge of the cover;
   wherein the first end of the first element is fixed in the chamber, the second end of the first element is suspended, and a portion of the first element is exposed from the opening of the chamber;
   wherein the second element and the third element are located on the outer edge of the cup body;
   wherein when the first end of the first element passes through the second element that blocks the first element, the second element causes deformation and vibrations of the first element, which produce a sound as to prompt that the cover is covering the specified location, and
   wherein the first element is parallel to a central axis of the cover.

2. The apparatus according to claim 1, a friction is produced when the first end of the first element passes through the second element, and the friction causes the first element to generate the vibrations.

3. The apparatus according to claim 1, wherein the first element produces a deformation when the first element is in contact with the second element, and the deformed first element needs to restore to no-deformation as to produce the vibrations.

4. The apparatus according to claim 1, wherein the second element and the third element are located on a skirt of the cup body and perpendicular to a central axis of the cup body.

5. The apparatus according to claim 4, wherein the second element and the third element are formed by a protrusion of the skirt.

6. The apparatus according to claim 4, wherein a length of the first element is greater than a height of the second element or the third element.

7. The apparatus according to claim 6, wherein the first element is of the same material as the second element or the third element, and wherein the length of first element deformation is greater than the height of the second and the third element.

8. The apparatus according to claim 4, wherein the cup body comprises a threaded structure, and the skirt is located below the threaded structure.

9. The apparatus according to claim 1, wherein the cover comprises three first elements, and the outer edge of the cup body comprises three second elements and three third elements corresponding to the three first elements, respectively.

10. The apparatus according to claim 1, wherein the collection chamber comprises a testing element, and the testing element is located in a groove of a base layer.

11. The apparatus according to claim 10, wherein a cross section of the collection chamber is of a triangular shape, and the collection chamber comprises three faces relying on the base layer.

12. The apparatus according to claim 1, wherein the liquid sample is a urine sample.

13. A method of detecting analyte in a liquid sample, providing the detection apparatus as claimed in claim 1, collecting the liquid sample into the collection chamber, contacting the liquid sample with the test strip, to detect analyte in the liquid sample.

\* \* \* \* \*